US009869851B2

(12) United States Patent
Halvorsen et al.

(10) Patent No.: US 9,869,851 B2
(45) Date of Patent: Jan. 16, 2018

(54) CENTRIFUGE FORCE MICROSCOPE MODULES AND SYSTEMS FOR USE IN A BUCKET OF A CENTRIFUGE

(71) Applicant: THE RESEARCH FOUNDATION FOR THE STATE UNIVERSITY OF NEW YORK, Albany, NY (US)

(72) Inventors: Kenneth A. Halvorsen, Glenmont, NY (US); Tony P. Hoang, Albany, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 491 days.

(21) Appl. No.: 14/530,434

(22) Filed: Oct. 31, 2014

(65) Prior Publication Data

US 2015/0122977 A1    May 7, 2015
US 2017/0139192 A9    May 18, 2017

Related U.S. Application Data

(63) Continuation-in-part of application No. 13/701,042, filed as application No. PCT/US2011/038716 on Jun. 1, 2011, now Pat. No. 9,354,189.
(Continued)

(51) Int. Cl.
G02B 21/00 (2006.01)
G01N 11/00 (2006.01)
G01N 15/14 (2006.01)

(52) U.S. Cl.
CPC ......... *G02B 21/0004* (2013.01); *G01N 11/00* (2013.01); *G01N 15/1436* (2013.01)

(58) Field of Classification Search
CPC ........... G02B 21/0004; G01N 15/1434; G01N 15/1436; G01N 11/00; G01N 2015/0053; G01N 2015/144; G01N 2015/1445
See application file for complete search history.

(56) References Cited

U.S. PATENT DOCUMENTS 6,143,183 A    11/2000    Wardwell et al.
6,654,102 B1   11/2003    Modares et al.
(Continued)

FOREIGN PATENT DOCUMENTS

EP    0123178 A2    10/1984
EP    0589556 A3    3/1994
(Continued)

OTHER PUBLICATIONS

Ken Halvorsen et al.: "Massively Parallel Single-Molecule Manipulation Using Centrifuge Force", Biophysical Journal, vol. 98, No. 11, Jun. 2, 2010, pp. 53-55, XP55005032.
(Continued)

*Primary Examiner* — Timothy Cleveland
(74) *Attorney, Agent, or Firm* — Reslin Rothenberg Farley & Mesiti P.C.

(57) ABSTRACT

A centrifuge force microscope module for use within a bucket of a centrifuge in measuring a characteristic of a sample under a centrifugal force and/or in monitoring a sample under a centrifugal force. The centrifuge force microscope module includes an electronics module and an optical module. The electronics module includes a housing removably disposable in the bucket of the centrifuge, and at least one of a power source and a connector operably connectable to a power source for powering the electronics module. The optical module is operable to receive and direct light from the sample. The optical module is releaseably connectable to the housing of the electronics module.

34 Claims, 29 Drawing Sheets

Related U.S. Application Data

(60) Provisional application No. 61/350,088, filed on Jun. 1, 2010.

(56) References Cited

U.S. PATENT DOCUMENTS

| | | | |
|---|---|---|---|
| 7,052,650 | B2 | 5/2006 | Strick et al. |
| 8,491,454 | B2 | 7/2013 | Wong et al. |
| 8,795,143 | B2 | 8/2014 | Wong et al. |
| 2003/0166262 | A1 | 9/2003 | Strick et al. |
| 2005/0051466 | A1* | 3/2005 | Carter ............ B04B 13/00 210/94 |
| 2006/0205581 | A1* | 9/2006 | Chammas ............ B04B 9/14 494/16 |
| 2007/0238598 | A1 | 10/2007 | Kim et al. |
| 2009/0118140 | A1 | 5/2009 | Suzara |
| 2010/0137120 | A1 | 6/2010 | Wong et al. |
| 2013/0130884 | A1 | 5/2013 | Wong et al. |
| 2013/0288349 | A1 | 10/2013 | Wong et al. |

FOREIGN PATENT DOCUMENTS

| | | |
|---|---|---|
| JP | 11-258081 | 9/1999 |
| WO | 2008112980 A2 | 9/2008 |
| WO | 2010065477 A2 | 6/2010 |
| WO | 2011/153211 A1 | 12/2011 |

OTHER PUBLICATIONS

Al Bitar L. et al.: "Tarsal Morphology and Attachment Ability of the Codling Moth Cydia Pomonella L. (Lepidoptera Tortricidae) to Smooth Surfaces", Journal of Insect Physiology, Pergamon Press, Oxford, GB, vol. 55, No. 11. Nov. 1, 2009, pp. 1029-1038, XP026613479.

Federle W. et al. L "Attachment Forces of Ants Measured With a Centrifuge: Better wax-runners' Have a Poorer Attachment to a Smooth Surface" Journal of Experimental Biology, vol. 203, No. 3, Feb. 3, 2000, pp. 505-512, XP002572371.

International Search Report, International Application No. PCT/US2009/066154 (published as WO/2010065477), 7-pages, dated Jul. 27, 2010.

International Search Report, International Application No. PCT/US2011/038716 (published as WO/2011153211), 3-pages, dated Aug. 29, 2011.

M. Vargas et al.: "A Centrifuge for Studies of Fluid Dynamics Phenomena in a Rotating Frame of Reference", Revista Mexicana De Fisica, vol. 8, No. 3, Jun. 1, 2002, pp. 255-266, XP55005142.

* cited by examiner

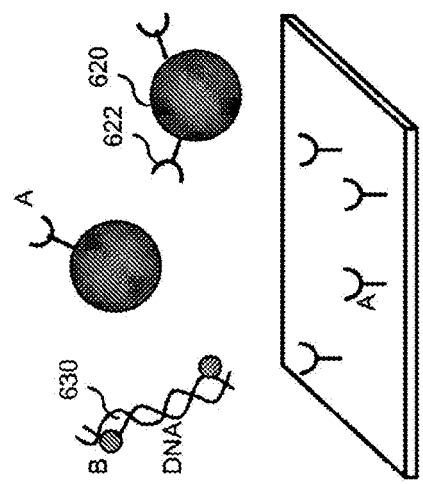
*FIG. 6B*
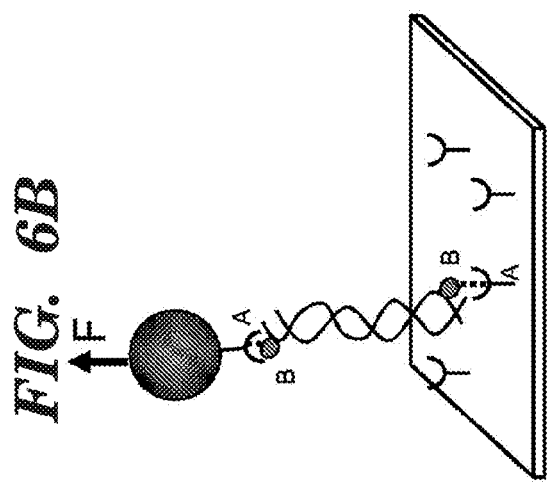
*FIG. 6D*
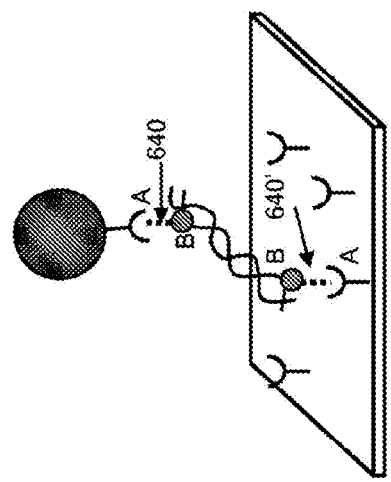
*FIG. 6A*
*FIG. 6C*

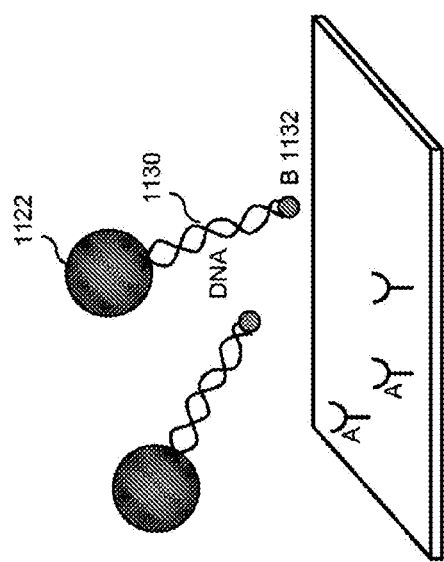
FIG. 11A
FIG. 11B
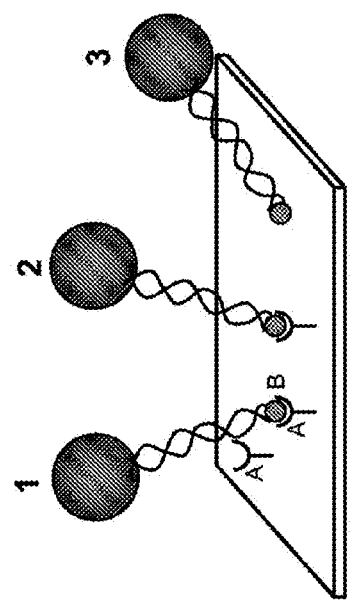
FIG. 11C
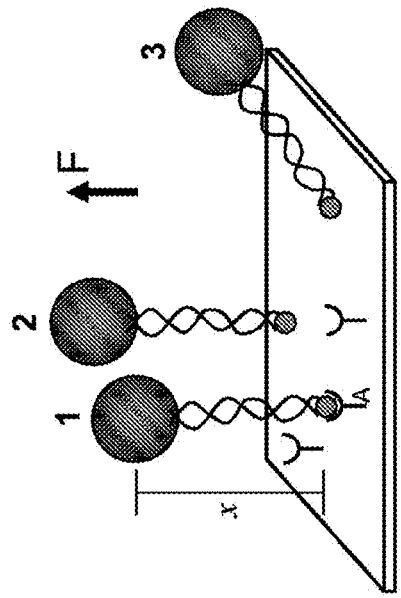
FIG. 11D

CENTRIFUGE FORCE MICROSCOPE MODULES AND SYSTEMS FOR USE IN A BUCKET OF A CENTRIFUGE

CROSS-REFERENCE TO RELATED APPLICATION(S)

This application is a continuation-in-part of U.S. patent application Ser. No. 13/701,042, filed Jan. 30, 2013, entitled "Apparatus For Measurement Of Spinning Forces Relating To Molecules,", which application is a national phase filing under 35 U.S.C. §371 of PCT International Application PCT/US2011/038716, filed Jun. 1, 2011, and published under PCT Article 21(2) in English as WO2011153211 on Dec. 8, 2011, which PCT application claims priority from U.S. Provisional Application No. 61/350,088, filed Jun. 1, 2010, the entire contents of these applications being incorporated herein by reference.

This application is related to U.S. application Ser. No. 12/326,279, filed Dec. 2, 2008, and entitled "Spinning Force Apparatus," the contents of which are incorporated herein by reference.

FIELD OF THE DISCLOSURE

This invention relates to measurement of forces relating to molecules.

BACKGROUND

The ability to quantify interactions between biomolecules is of great interest for scientific and medical research, as well as for drug development. Examples of measurable characteristics of a biomolecular interaction include the affinity (e.g., how strongly the molecules bind/interact) and the kinetics (e.g., rates at which the association and dissociation of molecules occur) of the interaction. Traditionally, such characteristics are measured in solution, using methods such as calorimetry, stop-flow imaging, or surface plasmon resonance. These bulk measurements are limited in many ways, including 1) they report only average behavior and thus may lose important details associated with metastable states and rare events, and 2) they measure chemistry in the absence of externally applied mechanical stress, which can be dramatically different from crowded and dynamic environments in living systems.

Recent development in single molecule measurement methods offers a different approach in quantifying molecular interactions by examining the behavior of individual molecules rather than measuring the properties of bulk solutions. This approach enables the observation of rare or fleeting events that can be obscured by ensemble averaging. The resulting detailed information of molecular transitions helps researchers to identify metastable states and to study the transitions rates and the chemical pathways between such states. Furthermore, heterogeneities between molecules in a population and within the behavior of a single molecule can both be quantified.

Currently, force probes that apply single molecule measurement methods include atomic force microscopes (AFM), optical traps, magnetic tweezers, biomembrane force probes, and flow chambers. Despite many advantages, these devices still have several limitations. For example, due to technical complexities, some systems require a large investment of money and time (e.g., optical trap systems typically cost $150 k or more). Additionally, molecular interactions are studied one molecule at a time in most cases. Statistical characterization of these interactions is therefore slow and painstaking, requiring hundreds or thousands of measurements which are typically performed in a serial manner.

SUMMARY

In a first aspect, the present disclosure provides a centrifuge force microscope module for use within a bucket of a centrifuge in measuring a characteristic of a sample under a centrifugal force and/or in monitoring a sample under a centrifugal force. The centrifuge force microscope module includes an electronics module and an optical module. The electronics module includes a housing removably disposable in the bucket of the centrifuge, and at least one of a power source and a connector operably connectable to a power source for powering the electronics module. The optical module is operable to receive and direct light from the sample. The optical module is releaseably connectable to the housing of the electronics module.

In a second aspect, the present disclosure provides a centrifuge force microscope module for use within a bucket of a centrifuge in measuring a characteristic of a sample under a centrifugal force and/or in monitoring a sample under a centrifugal force. The centrifuge force microscope module includes an electronics module and an optical module. The electronics module includes a housing removably disposable within the bucket of a centrifuge, a light source for illuminating the sample, a processor, and at least one of a power source and a connector operably connectable to a power source. The optical module is removably positionable in the housing and includes a detector operable to receive light from the sample, and at least one optical lens for focusing the light from the sample onto the detector. The power source is operable to power the light source, the detector, and the processor.

In a third aspect, the present disclosure provides the above-noted centrifuge force microscope modules wherein the electronics module includes an electrical contact for operably electrically grounding the centrifuge force microscope module through the bucket to the centrifuge.

In a fourth aspect, the present disclosure provides the above-noted centrifuge force microscope modules wherein the electronics module further includes a transmitter and/or a receiver, and the electronics module includes an electrical contact for operably electrically connecting the centrifuge force microscope module through the bucket to the centrifuge so that the bucket and/or the centrifuge act as an antenna.

In a fifth aspect, the present disclosure provides a method for measuring a characteristic of a sample under a centrifugal force and/or use in monitoring a sample under a centrifugal force. The method includes rotating the sample in the above-noted centrifuge force microscope modules in a bucket of a centrifuge about an axis to apply a centrifugal force on the sample, projecting light onto the rotating sample, detecting light emitted from the rotating sample, and at least one of measuring the characteristic of the sample under the centrifugal force and/or monitoring the sample under a centrifugal force.

In a sixth aspect, the present disclosure provides a method for operating a centrifuge force microscope system disposed in a bucket of a centrifuge for measuring a characteristic of a sample under a centrifugal force and/or for monitoring a sample under a centrifugal force. The method includes establishing a connection between a centrifuge force microscope module disposed in the bucket of the centrifuge and a remote computing unit, sending instructions from the remote computing unit to the centrifuge force microscope module regarding obtaining data from the sample, and transferring the obtained data from the centrifuge force microscope module to the remote computing unit.

In a general aspect, an apparatus for measuring a characteristic of a sample includes a sample measurement apparatus, which includes a light source configured to illuminate the sample; and a detector configured to receive light from the sample. The sample measurement apparatus is sized and dimensioned to fit within a centrifuge receptacle, the centrifuge receptacle coupled to a spindle configured to rotate the centrifuge receptacle to apply a force to the sample.

Embodiments may include one or more of the following. The sample measurement apparatus further comprises a lens configured to receive light from the sample, and wherein the detector is configured to receive light from the lens. The lens includes an aspheric lens. The sample measurement apparatus includes only one lens.

The apparatus further includes the centrifuge receptacle. The apparatus further includes a base disposed within the centrifuge receptacle and configured to be received the sample measurement apparatus. The centrifuge receptacle includes at least one of a centrifuge tube, a swing bucket, and a rotor. The centrifuge receptacle is a centrifuge tube having a volume of less than or equal to about 50 mL.

The sample measurement apparatus further includes a lens tube, wherein the light source, the lens, and the detector are disposed within the lens tube. The apparatus further includes a battery coupled to the centrifuge receptacle and electrically connected to the light source and the detector. The battery is disposed within the centrifuge receptacle.

The apparatus further includes a recording device coupled to the centrifuge receptacle, the recording medium configured to record a signal received from the detector. The recording device is disposed within the centrifuge receptacle.

The apparatus further includes a wireless communications module configured to wirelessly transmit a signal received from the detector. The apparatus further includes a computing device electrically connected to the detector. The computing device is external to the centrifuge receptacle. The detector is electrically connected to the computing device via a rotary joint.

The apparatus further includes a computing device external to the centrifuge receptacle. The detector is optically connected to the computing device via a fiber optic rotary joint.

The spindle forms part of a centrifuge. An optical axis of the sample measurement apparatus is substantially perpendicular to an axis of rotation of the centrifuge receptacle.

Among other advantages and features, the spinning force system and methods described herein can provide one or more of the following advantages.

A small-scale spinning force system uses a bench top centrifuge, which is standard equipment in many scientific laboratories. The use of standard equipment decreases the cost and increases the accessibility of the spinning force approach to molecular characterization. Furthermore, the components of the small-scale spinning force system are themselves relatively inexpensive.

The system and methods of operation can provide massively-parallel high-throughput single-molecule force measurements at a low cost. More specifically, rotation-induced forces (e.g., centrifugal forces and viscous drag forces) can be used to manipulate single molecules (e.g., proteins or DNAs) or molecular complexes (e.g., receptor-ligand protein pairs), enabling forces to be applied simultaneously to many subjects. Each subject can be observed directly and independently for true single-molecule detection. The efficiency of experiments can be improved, reducing the time to conduct an experiment from days to minutes. More than simply speeding up experiments, this efficiency also enables new experiments such as near equilibrium measurements that observe interactions with hour-long lifetimes, which would be unfeasible with sequentially collected statistics. Furthermore, with larger statistical sets more easily attainable, more detailed characterizations, model testing, and observations of population heterogeneity are possible. Parallel measurements can also be used to test families of interactions simultaneously (e.g., multiple drug candidates could be tested simultaneously against a target receptor).

The system and methods of operation can provide accurate force control in a wide range of directions and magnitudes. Through force control, the system and methods of operation can be used to quantify force dependent interactions, including measuring the force dependence of kinetic parameters (e.g., $K_{on}$ and $K_{off}$) and molecular subtleties which would be invisible from population averaging. Using this system, the mechanical properties of biomolecular complexes (e.g., compliances of DNAs and proteins) and cellular targets (e.g., elasticity of stress-bearing cells) can be studied, yielding valuable information into both the structure and the function of those subjects.

The centrifugal force field applied to a sample in the system and methods of operation describe herein is macroscopically uniform, stable without the need for active feedback, calibration-free, and dynamically controllable in an essentially deterministic way. Thus, a desired force history can be applied to an ensemble of single molecules without the need for active feedback. The force field conveniently couples to mass density, eliminating the possibility of radiative damage and expanding the range of systems that can be studied with force (e.g., beads or objects made of any material can be used, as long as they have a different mass density than their surroundings). Furthermore, by varying the bead type, bead size, and rotation speed, a wide range of forces, at least from sub-femtoNewtons to nanoNewtons, can be achieved.

The system and methods of operation can be conveniently integrated with various types of force probes to generate forces in multiple dimensions with high flexibility. For example, the system can be used in conjunction with optical traps, magnetic tweezers and/or microfluidic devices to generate a combination of forces (such as gradient and scattering forces, magnetic forces, hydrodynamic forces, and centrifugal forces). Each force can be applied to a sample in a different direction, with a different magnitude, and/or at a different test stage.

The system and methods of operation can also be conveniently integrated with various imaging techniques to provide real-time observation with high temporal and spatial resolution. For example, using interference techniques and diffraction analysis, the position of individual particles in a sample can be ascertained with sub-nanometer accuracy. Also, fluorescent imaging enables visualization of subtle molecular transitions during experiment. Moreover, using video tracking by high-speed CCD cameras, molecular events can be detected on the scale of microseconds.

The systems and methods described herein are also more cost effective and simpler to use than other common methods of molecular spectroscopy. The material cost of a spinning force system is generally less than the cost of a typical laboratory microscope. Furthermore, experiments using this system are straightforward, with a pre-preprogrammed force protocol, minimal setup, and little or no need for user intervention.

Other features and advantages of the invention are apparent from the following description and from the claims.

BRIEF DESCRIPTION OF THE DRAWINGS

FIGS. 6A-6D are schematic representations of another procedure for preparing a sample to be measured by the spinning force system of FIG. 1.

FIGS. 11A-11D are schematic representations of a procedure for preparing a sample to be measured by the spinning force system of FIG. 1.

DETAILED DESCRIPTION

1 System Overview

Figure 1:
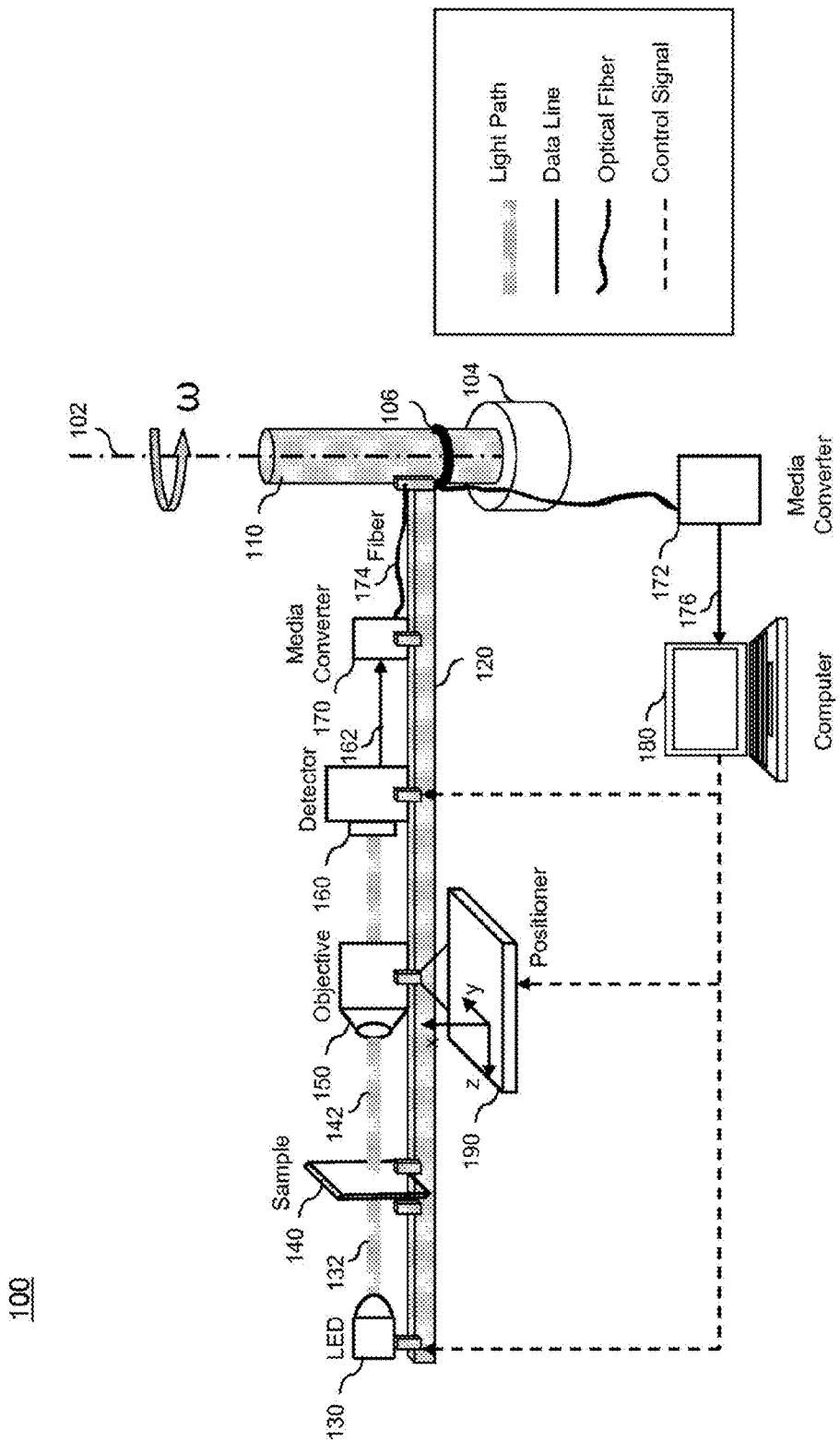
FIG. 1 is a schematic representation of one embodiment of a spinning force system.

Referring to FIG. 1, a spinning force system 100 includes a rotary arm 120 mechanically coupled to a rotary stage 110 (for instance, part numbers ADRT-150 and CP20, Soloist available from Aerotech (Pittsburgh, Pa.)) configured to rotate about a central axis 102 at an adjustable angular velocity ω. Rotary stage 110 is housed and supported on a stationary base 104 immobilized on a platform (not shown) such as a vibration-free optical table. The motion of rotary stage about central axis 102 is computer controlled.

Rotary arm 120 extends radially outward from central axis 102 to support a set of optical, mechanical, and electrical components for detecting characteristics (e.g., motion, optical, and geometric characteristics) of a sample 140 to be measured by system 100. These components include, for example, a light source 130, an objective 150, a light detector 160, and a media converter 170. In operation, these components are moved by rotary arm 120 to rotate about central axis 102 at the same angular velocity ω. Rotary arm 120 may also carry one or more positioning elements (e.g., adjustment screws for coarse adjustment, such as screw AJS100-02H available from Newport (Irvine, Calif.) and electromechanical stages such as piezoelectric positioners for fine adjustment, such as piezo AE0505D08F available from Thorlabs (Newton, N.J.)) for adjusting the position of each component coupled to arm 120. Examples of positioning elements will be described in greater detail below.

In this example, light source 130 is mounted at a distal end of rotary arm 120 for emitting a light beam 132 to illuminate a selected region of sample 140. Examples of light source 130 suitable for use in system 100 include various types of lamps (such as LED bulbs (e.g., LED lamp LED528E available from Thorlabs) and xenon arc lamps) and lasers (such as single- and multiple-wavelength lasers). Light source 130 may also include a set of optical components such as lenses, mirrors, and filters (not shown) for controlling the characteristics of its outgoing beam 132. For example, a condenser with diaphragms may be used for tuning the emission intensity of beam 132, and a color filter may be used for transmitting light at only selected wavelengths.

Sample 140 is mounted onto rotary arm 120 with a sample holder (not shown) fastened to the arm. Depending on the particular implementation, sample 140 may include an acrylic sample chamber (not shown) in which experiment subjects (such as cells, biomolecules, and DNA strands) are sealingly contained. The sample chamber may consist of two parallel cover glasses separated by a 1 mm o-ring, forming an enclosed volume that can be filled with buffer and beads. In some implementations, sample 140 is oriented such that the surfaces of the cover glasses are aligned in parallel to central axis 102. When rotary arm 120 rotates, the contents of sample 140 experience a centrifugal force normal to the cover glasses. In other implementations, sample 140 is oriented at a selected (and possibly adjustable) angle with respect to central axis 102, enabling the centrifugal force to be applied in any given direction.

Light beam 142 exiting sample 140 is received by objective 150 to produce a real image of the illuminated region of sample 140. The optical characteristics of objective 150 (e.g., magnification and numerical aperture) are selected depending on the particular implementation. For example, a 20× air-immersion objective may be used for applications that require a wide field of view, whereas a 100× oil-immersion objective may be preferred for applications that require a high spatial resolution.

Preferably, the relative position of objective 150 with respect to sample 140 is adjustable in three dimensions (x-, y- and z-directions shown in the figure), allowing images of different regions of the sample to be collected at various focal depths. In this example, objective 150 is staged on a piezoelectric positioner 190, which can be translated along each of the x-, y-, and z-directions by an external control signal (e.g., provided by a computer). In other examples, sample 140 (instead of objective 150) may be staged on positioner 190 for linear translation in those three dimensions.

Images formed by objective 150 are received by detector 160 and subsequently converted into electronic signals 162. One example of a detector suitable for use is a charge-coupled device (CCD), such as a 12-bit 5 megapixel CCD camera (e.g., part number GC 2450 available from Prosilica (Newburyport, Mass.)). Another example of a suitable detector is a CMOS detector. Preferably, detector 160 is capable of acquiring successive images at a speed sufficiently fast to enable video tracking of sample 140 at a high temporal resolution (e.g., 1 kHz). In some examples, light from objective 150 is first transformed through an intermediate optical system (not shown) before reaching detector 160. The intermediate optical system may include one or more elements such as lenses, filters, polarizers, and pinholes.

Electronic signals 162 from detector 160 are delivered, for example, using electrical, optical, or wireless transmission means, to be passed onto a computer 180. In this example, signals 162 are transmitted sequentially through an electronic-to-optical media converter 170, an optical fiber 174, and an optical-to-electronic media converter 172. Exemplary media converters are available from IMC Networks, Foothill Ranch, Calif. (part numbers 855-10734 and 855-10735). Both media converter 172 and computer 180 are positioned on a stationary platform (not shown). Using proper interfacing software, computer 180 decodes electronic signals 176 from media converter 172 to reproduce images of sample 140 on a screen. Optionally, optical fiber 174 is coupled to rotary stage 110 through a fiber optic rotary joint (not shown; e.g., part number MJX-155-28-SC available from Princetel, Pennington, N.J.), which can be further integrated into an electrical slipring 106 (e.g., part number SRF24 available from Princetel) of rotary stage 110. Power for detector 160, media converter 174, light source 130, and positioner 190 may be transmitted through slipring 106, allowing dynamic control of these components during rotation of system 100.

Computer 180 is used for viewing and processing images of sample 140. In addition, computer 180 is also configured to provide various control signals to control individual components of spinning force system 100. For example, computer 180 may be coupled to an electric motor (not shown) for controlling a rotational drive force to change the angular speed ω of rotary stage 110. Computer 180 may also be coupled to a positioning device (not shown) for adjusting a distance between light source 130 and sample 140, or coupled to positioner 190 for translating objective 150 in each of x-, y-, and z-directions to select detection regions and to control focal depth. Computer 180 may also be configured to control the optical characteristics of light source 130 (e.g., the brightness and the frequency range of output beam 132) as well as the image acquisition variables of detector 160 (e.g., readout rate, integration time, and electronic gain). Additionally, computer 180 may provide control signals based on previously acquired data, enabling real-time feedback control.

2 Operation 2.1 Force Application

Figure 2B:
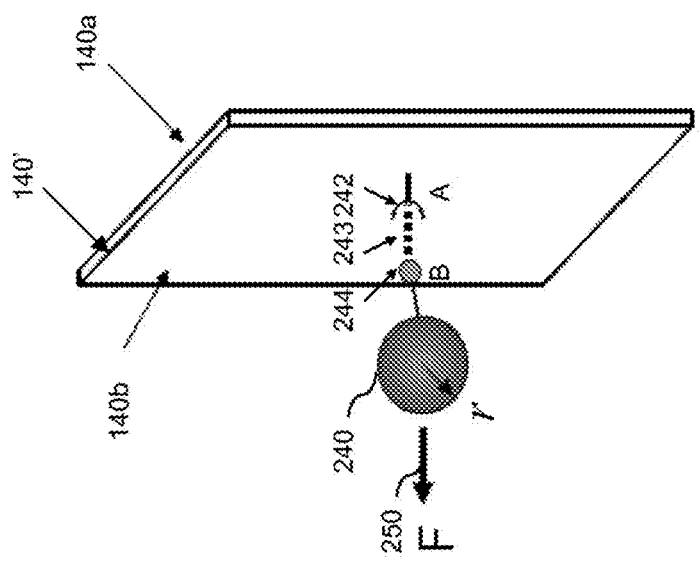
FIG. 2B shows a centrifugal force applied to the sample of FIG. 2A.
Figure 2A:
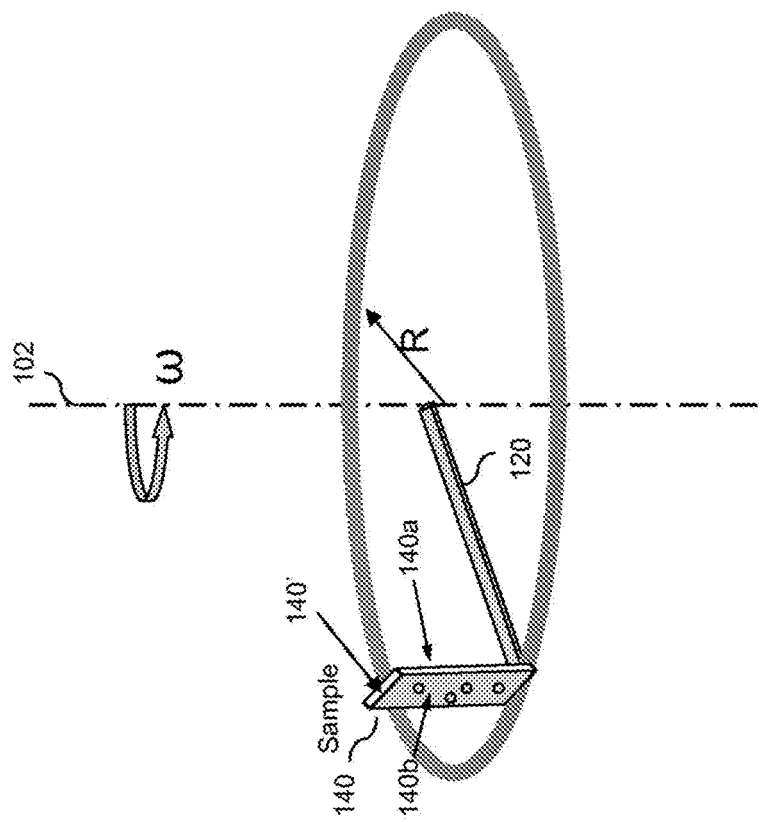
FIG. 2A is a schematic representation of a sample coupled to the spinning force system of FIG. 1.

Referring to FIGS. 2A and 2B, when rotary arm 120 is in operation, sample 140 rotates at an angular velocity ω and at a distance R from the center of axis 102. For illustrative purposes, in this example, sample 140 includes a cover slip 140' having an inner surface 140a and an outer surface 140b with respect to axis 102. Both surfaces are aligned in parallel with axis 102. A particle 240 (e.g., a bead) adheres to outer surface 140b through a chemical bond 243 formed between molecule A 242 and molecule B 244. In this example, molecule A is a receptor chemically linked to outer surface 140b, and molecule B is a ligand chemically linked to particle 240. (The techniques and methods for forming such linkages will be described in greater detail below).

When particle 240 undergoes circular motion, a centripetal force F is exerted on the particle, as defined by the following equation:

$$F = \frac{mv^2}{R} \tag{1}$$

where F is the net centripetal force, m and v are the mass and the linear velocity of the particle, respectively, and R is the distance of the particle from rotation axis 102. In a rotating reference frame in which orbiting particle 240 appears stationary, particle 240 experiences an inertial centrifugal force equal to F in a direction perpendicular to outer surface 140b and away from central axis 102 (shown by arrow 250). In some examples where particle 240 is a spherical bead in solution with radius r and relative density ρ, rewriting equation (1) in terms of angular velocity ω yields:

$$F = \frac{4\pi\rho r^3 R\omega^2}{3} \qquad (2)$$

When sample 140 rotates about axis 102 at a very low speed, centrifugal force F is countered by the interaction force of chemical bond 243, allowing particle 240 to continue to adhere to surface 140b. As the rotational speed ω rises, the increasing magnitude of centrifugal force F causes bead 240 to move with respect to surface 140b. The characteristics of the relative motion (e.g., the root-mean-square displacement or the direction of the motion) can be monitored and analyzed to quantify certain chemical and/or mechanical properties of bond 243 (e.g., properties associated with its transitional states and conformational changes). The increasing F may also cause the rupture of chemical bond 243, at which point, particle 240 is released from surface 140b. The magnitude of centrifugal force F at the particle release indicates the rupture force of chemical bond 243.

During operation, the magnitude of centrifugal force F can be controlled, for example, by adjusting the angular velocity ω of rotary arm 120. For instance, sample 140 can be subjected to multiple cycles of force application in which the centrifugal force on particle 240 is increased and/or decreased through step changes in angular velocity ω.

In addition to changing the angular velocity ω, it is also possible to change the radius of rotation R either statically or dynamically by changing the sample position relative to the axis of rotation. For example, in system 100, sample 140 may be mounted to an adjustable rotary arm with extendible length, or staged on a positioner that can be translated in a radial direction with respect to central axis 102.

In cases where particle 240 is a spherical bead, the centrifugal force F can also be varied by changing one or more of the particle characteristics ρ and r shown in equation (2). For example, microspheres are commercially available in a wide range of materials and sizes (see Table 1 below). By conjugating subjects of study (e.g., molecules or cells) to selected microspheres, the centrifugal force applied to the microspheres (and translated to the subject) can be varied based on bead properties. In addition, the degree of monodispersity of beads can control the range of forces applied for a given spin. For instance, a highly monodisperse sample (e.g., using beads of substantially the same size and properties) may cause all beads to experience the same force, while a polydisperse sample (e.g., using beads of various sizes and/or properties) would have a wide range of forces being applied. Moreover, ρ of particle 240 can also be altered by changing the density of the buffer solution. Furthermore, the geometry of the sample chamber can be varied to control the effects of fluid flow, which can add hydrodynamic forces to immobilized particles in the chamber.

TABLE 1

The materials and sizes of common beads

| Bead Material | Specific Density (g/cm³) | Size Range (µm) |
| --- | --- | --- |
| Borosilicate | 1.5 | 1-100+ |
| Polystyrene | 0.05 | 0.05-100+ |
| Silica | 1.2 | 0.01-100 |
| Gold | 18.3 | 0.002-0.25 |
| Melamine | 0.51 | 0.5-10 |
| Iron Oxide | 4.24 | 1-10 |

With proper parameter selection, the force applied to particle 240 can span 9 orders of magnitude, ranging from microNewtons (e.g., r=10 µm, ρ=1.5 g/cm³, R=500 mm, ω=100 Hz) to femtoNewtons (e.g., r=1 µm ρ=0.05 g/cm³, R=250 mm, ω=2 Hz).

The direction of the centrifugal force F can also be controlled. In some examples, sample 140 may be configured in an orientation perpendicular to rotational axis 102, resulting in a centrifugal force F along surface 140b. In other examples, sample may be configured to form a selected angle with respect to rotational axis 102 so that centrifugal force F may be applied in any given direction. For instance, a compressive (rather than tensile) force can be applied to particle 240 if the particle is positioned on inner surface 140a (rather than outer surface 140b) of the cover glass. For particular implementations, it may be desirable to place sample in a parallel position with respect to rotation axis 102 because pulling particle 240 away from surface 140b reduces the likelihood of the particle forming new interactions with unoccupied binding sites of molecule A on the surface 140b.

In addition to centrifugal force F, other types of forces can also be applied to particle 240 through spinning. For example, if particle 240 is contained in a chamber filled with a liquid medium, the rotation of sample 140 can generate regional flows that exert a viscous drag force D to particle 240. The direction of the drag force depends on factors such as the geometry of the chamber and the orientation of the sample. The magnitude of the drag force depends on factors such as the viscosity and the temperature of the liquid medium, the size of the particle, and the rotational velocity and acceleration of the sample.

2.2 Observing Motion Characteristics

In spinning force system 100, motion of particle 240 (e.g., displacement caused by molecular folding, unfolding or rupture of bond 243) can be observed by video tracking methods (e.g., by taking successive images of the particle at a high temporal resolution). Because light source 130, sample 140 and objective 150 rotate together at the same angular velocity ω, these three components appear stationary to each other in a rotating reference frame. Therefore, images of particle 240 can be formed using traditional imaging techniques, including transmitted- or reflected-light techniques and fluorescence techniques.

Figure 3A:
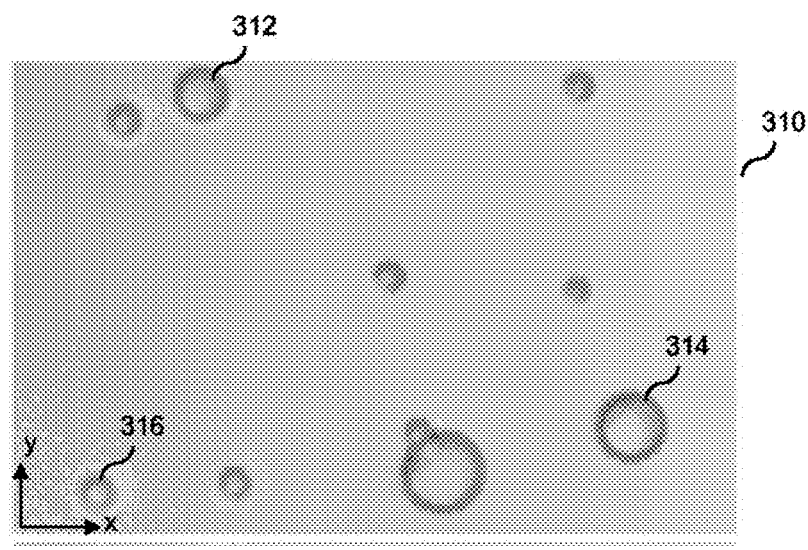
FIGS. 3A and 3B are transmitted light images of a sample generated at two different focal depths, respectively.
Figure 3B:
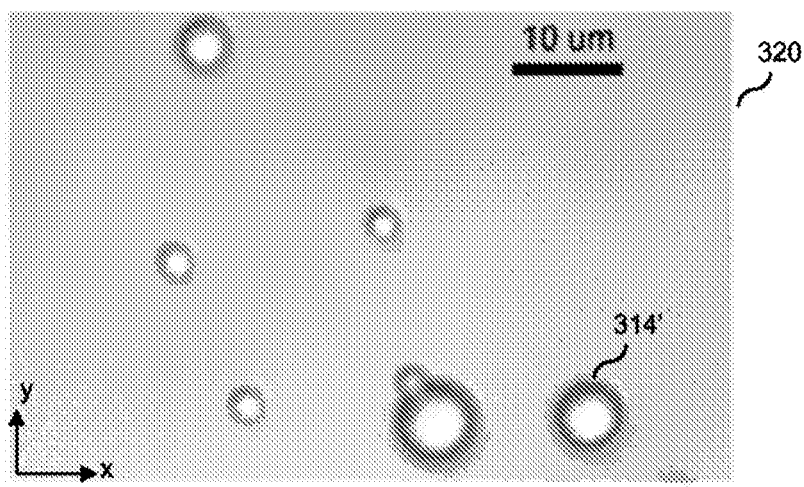

Referring to FIGS. 3A and 3B, images 310 and 320 are transmitted-light images of the same region of sample 140 produced at two different focal depths, respectively. In this example, sample 140 contains multiple beads (appearing, for example, as circular objects 312, 314 and 316 in image 310) near surface 140b. The location of each bead in the images represents the lateral position of the bead (e.g., along x- and y-axes of FIGS. 1, 3A and 3B). The image pattern of the bead (e.g., the size, the sharpness and the ring pattern of circular objects 312, 314 and 316) indicate the focal depth, namely, the distance of the bead from objective 150 (e.g., along z-axis of FIG. 1). This focal depth can be used to represent the relative position of the bead above surface 140*b*.

By analyzing the lateral position and the image pattern of individual beads, the movement of the beads with respect to time can be characterized in a three-dimensional space. Such characterization enables the quantification of the affinity and the kinetics of chemical bond 243 that links the bead to surface 140*b*. For example, before spinning, the position of objective 150 can be adjusted such that particle 240 situates in the objective's focal plane, resulting in a sharp in-focus image when the particle adheres to surface 140*b*. During spinning, if the centrifugal force F is sufficiently strong to cause bond rupture, particle 240 is quickly (typically at a speed of microns/s or faster) pulled away by centrifugal force F from surface 140*b* (e.g., along z-axis of FIG. 1). The escape of the particle from the objective's focal plane can be observed by changes in the characteristics of the detected image that are correlated with changes in focal depths. For example, a disappearance or blurriness of a circular pattern representing particle 240 (e.g., similar to the disappearance of object 316 from image 320 or the blurriness of object 314' in image 320) indicates that the particle is being pulled away from the focal plane of objective 150, e.g., as a result of bond rupture. Once bond rupture is identified, the bond force can be computed based on the magnitude of centrifugal force F, as defined in equation (1) or (2).

In examples where bond rupture is not necessarily observed or desired, detecting particle movement can provide valuable information about the compliance of a molecular tether that includes bond 243. For example, the displacement of particle 240 subjected to varying amplitude of centrifugal force F can be used to compute the elastic modulus of the molecular tether, and possibly to map the force dependency of such modulus. Also, stepwise changes in the position of particle 240 may indicate the transitions between molecular states that are associated with conformational changes of a chemical bond. For example, a bead that remains tethered but moves suddenly away from the cover glass can signify unfolding of a protein domain.

The transmitted light imaging technique described above can easily provide a spatial resolution along the optical axis of about 100 nm for observation. In certain implementations where a higher resolution is desirable, more sophisticated imaging and image processing techniques can also be applied. For example, by using advanced techniques such as using transmitted or reflected light interference patterns of individual beads, the position of a bead relative to surface 140*b* can be determined with sub-nanometer accuracy.

Figures 4A, 4B, 4C:
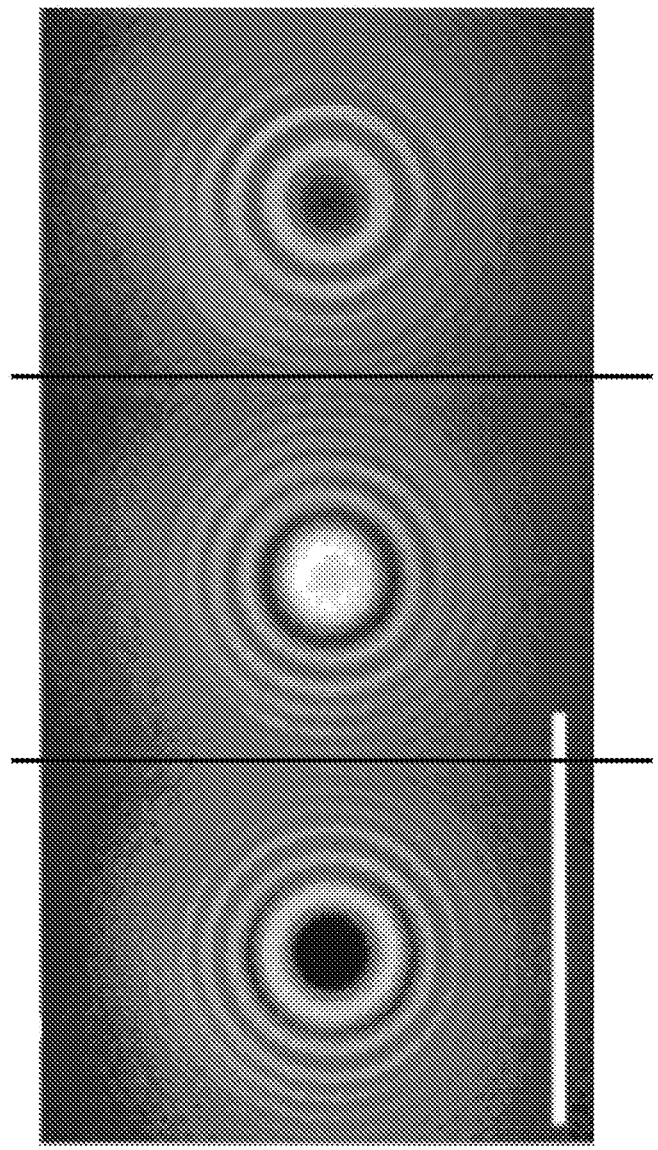
FIGS. 4A-4C show the interference patterns of a sample imaged by a reflection interference contrast microscope at three different heights, respectively.

Referring to FIGS. 4A-4C, the interference patterns of a single particle imaged by a reflection interference contrast microscope (RICM) at three different heights are shown, respectively. In these figures, the alternation of dark and bright fringes as well as the intensity and the size of each fringe can be decoded to reconstruct the height profile of the particle with a sub-nanometer axial resolution. (The white bar shown in these figures represents 10 μm). An example of particle tracking using the RICM technique is described by Heinrich et al., in Fast Three-Dimensional Tracking of Laser-Confined Carrier Particles, published in Langmuir, 24(4):1194-1203, 2008, the contents of which are incorporated herein by reference.

In addition to the aforementioned imaging techniques, fluorescence techniques can also be implemented alone or together with transmitted/reflected light techniques to enhance resolution and to enable visualization of subtle molecular transitions during experiment.

3a Small-Scale Spinning Force System

Figure 14:
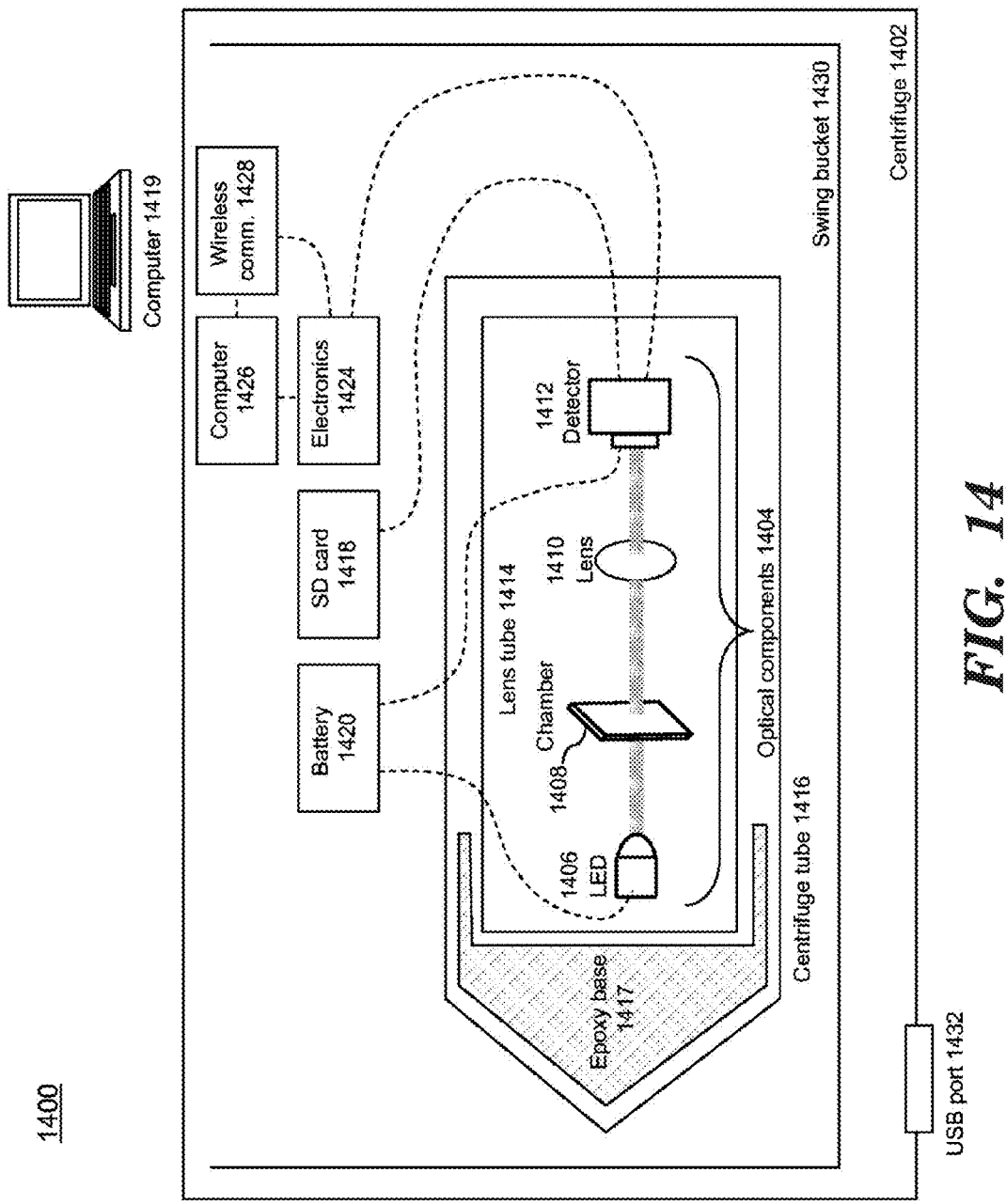
FIG. 14 is a block diagram of a small-scale spinning force system.

Referring to FIG. 14, in an alternate embodiment, a small-scale spinning force system 1400 uses a standard laboratory centrifuge 1402 to provide rotational force for the study of molecular interactions. Spinning force system 1400 includes optical path components 1404, including an LED light source 1406 (e.g., an LED525E available from Thorlabs), a sample chamber 1408, a lens 1410 used for magnification, and a detector 1412, such as a consumer-grade 5 Megapixel CCD camera or a CMOS (complementary metal-oxide-silicon) camera. Detector 1412 is, for instance, a VholdR (Seattle, Wash.) Contour HD CCD camera. Lens 1410 may be an aspheric lens (such as lens C230TME-A available from Thorlabs) that is sufficiently aberration-free to allow only a single lens to be used; alternatively, lens 1401 may be a multi-lens microscope objective. In some cases, optical path components 1404 act as a roughly 10× microscope. In some embodiments, a lens is not used and the detector 1412 receives light directly from sample chamber 1408.

Optical path components 1404 are aligned within a lens tube 1414, such as a ½ inch diameter SM05 lens tube (Thorlabs), placed inside of a centrifuge receptacle. In some embodiments, the centrifuge receptacle is a standard centrifuge tube 1416, such as a plastic centrifuge tube having a volume of, e.g., 50 mL, 15 mL, 1.5 mL, or another volume. A cone-shaped base 1417 formed from molded epoxy fits snugly at the end of centrifuge tube 1416. A hole is drilled in the center of epoxy base 1417 and the LED end of the lens tube 1414 is inserted into the hole in the base 1417, stabilizing the position of the optical components 1404 within centrifuge tube 1416. In some cases, such as that shown in FIG. 14, centrifuge tube 1416 is placed within a swing bucket 1430 of centrifuge 1402; in other cases, centrifuge 1402 is configured to accept centrifuge tube 1416 in a centrifuge tube holder (not shown). In an alternate embodiment, the centrifuge receptacle is itself a standard centrifuge bucket, e.g., a bucket configured to hold multiple centrifuge tubes. In still other embodiments, the centrifuge receptacle may be a modified centrifuge rotor.

Figure 15:
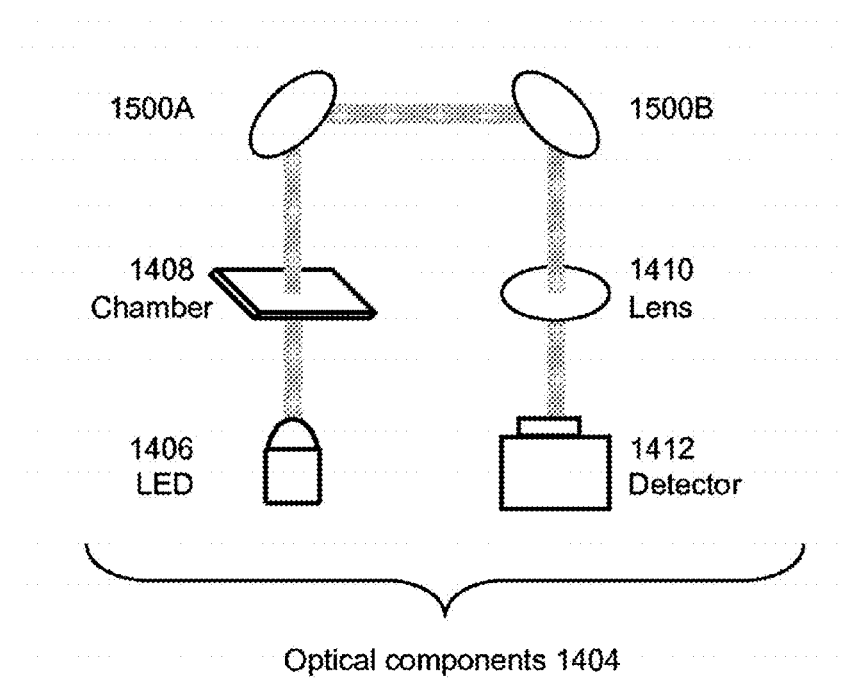
FIG. 15 is a block diagram of an alternative arrangement of optical components in a small-scale spinning force system.

Referring to FIG. 15, in an alternative embodiment, for a more compact setup, the optical path of optical path components 1404 is bent by two 45 degree mirrors 1500*a*, 1500*b*.

Referring again to FIG. 14, a memory device, such as a solid-state secure digital (SD) card 1418, records video signals received from CCD camera 1412 representative of images of the sample formed by lens 1410. The video images recorded on SD card 1418 can be analyzed by an external computer 1419 after an experiment is completed. Both camera 1412 and LED 1406 are powered by a small battery 1420, such as a lithium polymer battery. In some embodiments, SD card 1418 and battery 1420 are placed in swing bucket 1430 along with centrifuge tube 1416, with electrical connections between SD card 1418 and camera 1412 and between battery 1420 and both LED 1406 and camera 1412. Electronic components 1424 (e.g., a circuit board) that control camera 1412 are also positioned in swing bucket 1430. In this configuration, SD card 1418, battery 1420, and electronic components 1424 rotate along with the optical path components 1404, but are not subject to size constraints that would be imposed by assembly within centrifuge tube 1416. In other embodiments, SD card 1418, battery 1420, and electronic components 1424 are placed in another centrifuge tube (not shown), which may be positioned within the swing bucket 1430 along with centrifuge tube 1416, or which may be placed in another centrifuge tube holder. In still other embodiments, SD card 1418, battery 1420, and electronic components 1424 are small enough to be positioned within centrifuge tube 1416. A port 1432, such as a Universal Series Bus (USB) port, is included in centrifuge 1402 to enable computer control of the rotation.

In some embodiments, an onboard computer 1426 (e.g., a small computer available from gumstix, Portola Valley, Calif.) is placed in the centrifuge tube 1416 or in the modified swing bucket 1422. The onboard computer is capable of locally analyzing the video received from CCD camera 1412; the results of the analysis are stored on SD card 1418. In other embodiments, a wireless communication device 1428 is used in addition to or in place of SD card 1418 so that the video feed from the detector can be transmitted in real time and analyzed with a remote computer. Alternatively, the wireless communication device communicates with the onboard computer such that analyzed results can be transmitted in real time.

Figure 16:
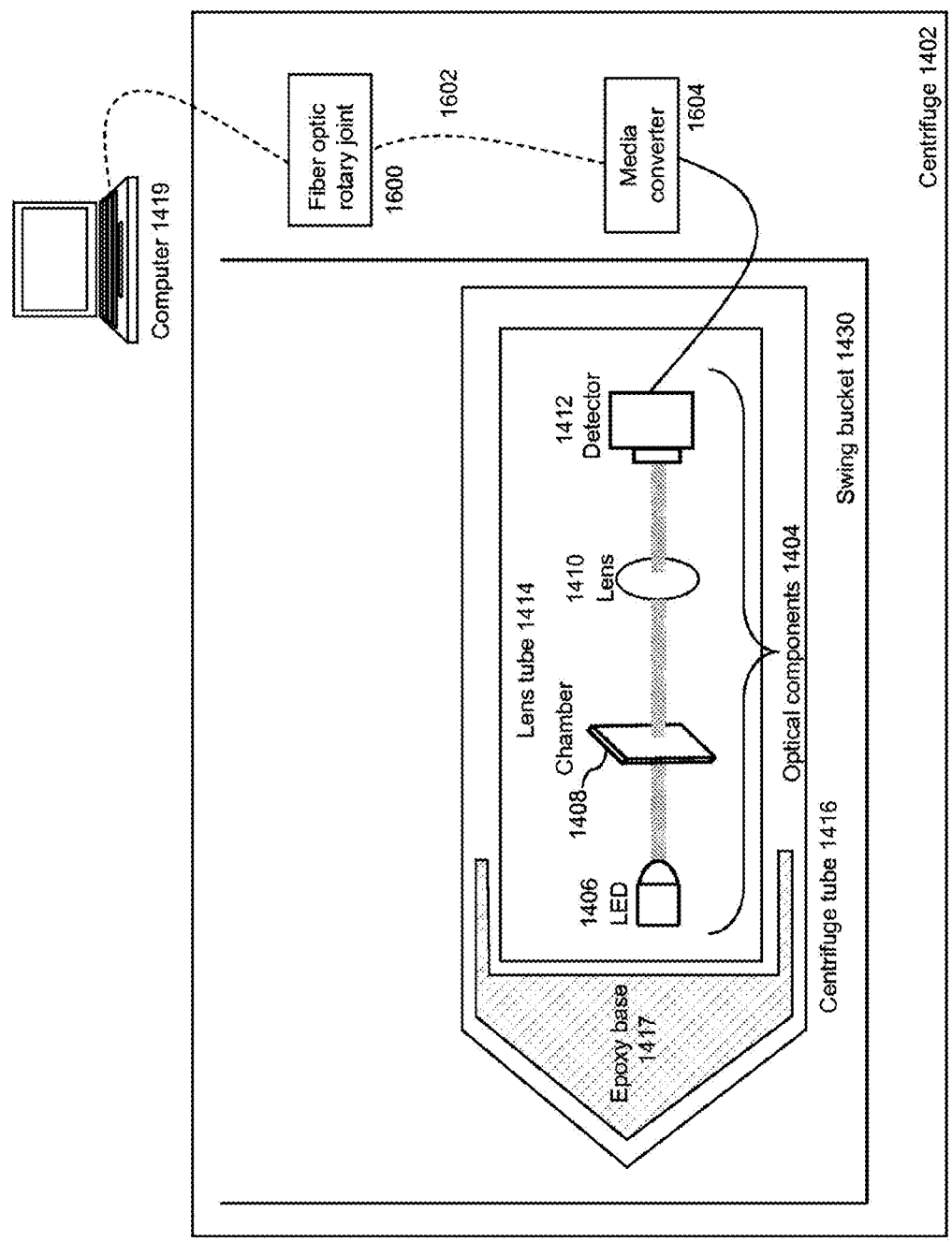
FIG. 16 is a block diagram of an alternative embodiment of a small-scale spinning force system.

Referring to FIG. 16, in still other embodiments, a fiber optic rotary joint 1600 integrated into centrifuge 1402 enables high speed communications between the standard laboratory environment (i.e., computer 1419) and the rotating sample. Data is transmitted from detector 1412 to an Ethernet-to-fiber media converter 1604 and then to external computer 1419 via fiber optic cable 1602 passing through fiber optic rotary joint 1600. Power for the electronic components in centrifuge tube 1416 may also be transmitted in a similar fashion, allowing dynamic control of these components during rotation of the small-scale system.

The principle of operation of small-scale spinning force system 1400 is similar to the operating principle of the spinning force system 100 described above. In spinning force system 1400, sample chamber 1408 is loaded with functionalized microspheres (e.g., 3 μm latex beads coated with molecule "A") and a functionalized cover slip (e.g., a glass cover slip coated with molecule "B"). The "A"-functionalized beads are brought into contact with the "B"-functionalized cover slip for a short time, for instance by turning centrifuge tube 1416 upside down. The lens tube 1414 and other components, such as SD card 1418, battery 1420, and electronic components 1424, are secured within centrifuge tube 1416 and/or swing bucket 1422. CCD camera 1412 is enabled such that video recording to the SD card 1418 is initiated. The centrifuge is properly balanced, if necessary, and rotation is started. Once the centrifuge is spinning, the "A"-functionalized particles will experience a force away from the "B"-functionalized cover slip. As described above, some particles bound to the cover slip via A-B molecular complexes will separate from the cover slip at various times; this time signature reveals the force-dependent dissociation of the A-B complex. Video analysis of the resulting data is performed after centrifugation is completed using particle detection techniques described herein.

3b Centrifuge Force Microscope (CFM) System

Figure 17:
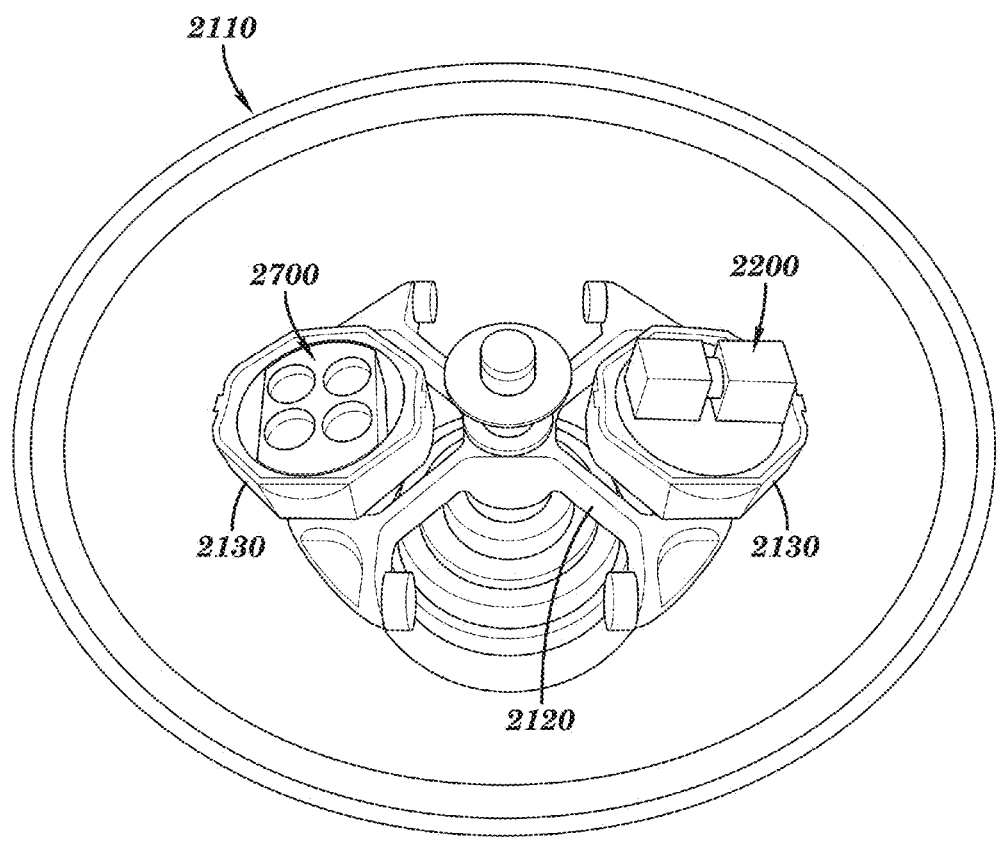
FIG. 17 is a perspective view of an embodiment of a centrifuge force microscope module and an embodiment of a counterweight module in accordance with aspects of the present disclosure disposed in a centrifuge.

Referring to FIG. 17, in one embodiment, a centrifuge force microscope (CFM) module 2200 and one embodiment of a CFM counterweight module 2700 in accordance with aspects of the present disclosure may be used in a conventional laboratory centrifuge 2110, such as a bench top centrifuge with a metal swing bucket rotor 2120, to provide rotational force for the study of molecular interactions. For example, CFM module 2200 and counterweight module 2700 may be disposed in respective buckets 2130 and disposed opposite from each other. FIG. 17 illustrates the CFM module and CFM counterweight module with the centrifuge at rest. When the centrifuge is operated the bottoms of the buckets rotate outwardly. A suitable centrifuge may be a Sorvall X1R centrifuge with the TX-400 swinging bucket rotor, where the buckets have an inner diameter of 80 mm.

Figure 18:
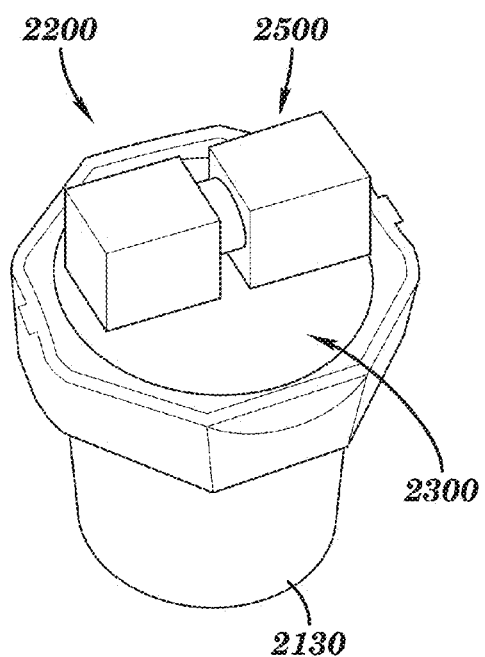
FIG. 18 is an enlarged perspective view of the centrifuge force microscope module of FIG. 17 having an electronics module and an optical module.

As shown in FIG. 18, CFM module 2200 may include, among other aspects, an electronics module 2300 and an optical module 2500 that fits within bucket 2130. At least some of the outer surface portions of the electronics module may be configured to the contour and provide a snug fit with at least some of the inner surface portions of the conventional bucket. CFM module 2200 may provide a compact design of the various optical and electrical components which components may be easily and readily accessed, assembled, and disassembled by a user in the study of molecular interactions. It will be appreciated that a CFM module may include differently sized rings to enable the CFM module to fit other size centrifuge buckets.

Figure 19:
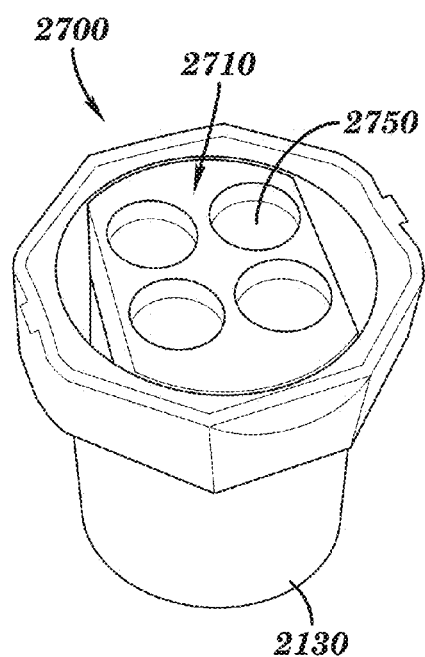
FIG. 19 is an enlarged perspective view of the counterweight module of FIG. 17 having a plurality of holders and weights.

As shown in FIG. 19, CFM counterweight module 2700 may include one or more holders 2710 and one or more weights 2750. At least some of the outer surface portions of the holders may be configured to the contour of at least some of the inner surface portions of the bucket. As described in greater detail below, the counterweight module may be designed to allow a user to assemble and readily match the mass and center of mass of the counterweight module with that of the CFM module.

Figure 20:
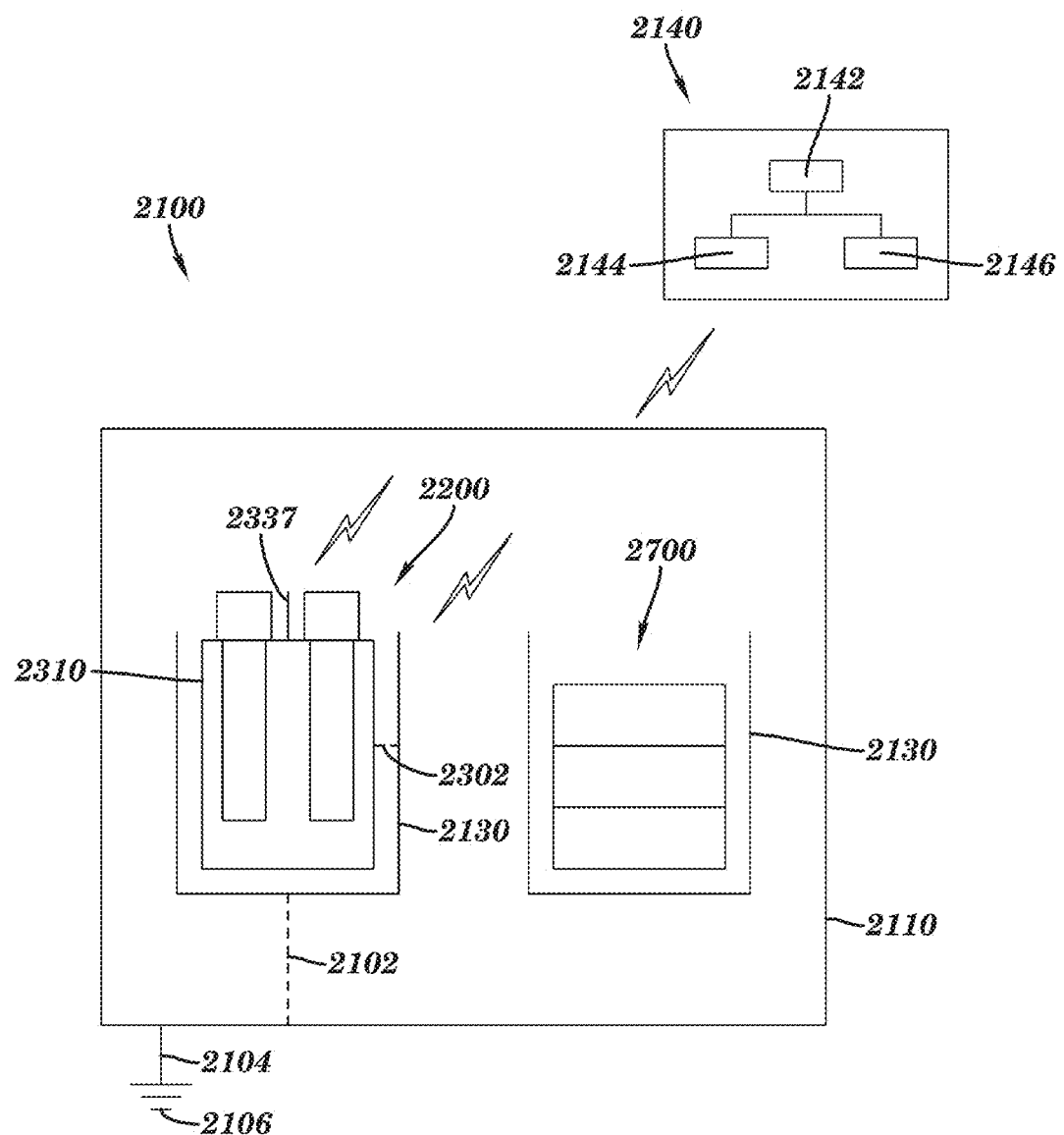
FIG. 20 is a block diagram of a centrifuge force microscope system employing the centrifuge force microscope module and a counterweight module of FIG. 17.

With reference to FIG. 20, a centrifuge force microscope system 2100 in accordance with aspects of the present disclosure may include CFM module 2200, counterweight module 2700, centrifuge 2110, and a computing unit 2140. In an aspect of the present disclosure, as described in greater detail below, electronics module or CFM module 2200 may be operably electrically grounded via an electrical pathway 2302 to bucket 2130, and bucket 2130 through an electrical pathway 2102 to centrifuge 2110, and centrifuge 2110 through an electrical pathway 2104 to a ground 2106. In another aspect of the present disclosure, as described in greater detail below, CFM module 2200 further may comprise a transmitter or transceiver (not shown in FIG. 20), and operably electrically connected to an antenna 2337 for wireless communication with computing unit 2140, and/or operably electrically connected via electrical pathway 2302 to bucket 2130 which bucket may act as an antenna for wireless communication with computing unit 2140, and/or operably electrically connected via electrical pathway 2302 to bucket 2130 and electrical pathway 2102 to centrifuge 2110 which bucket and/or centrifuge may act as an antenna for wireless communication with computing unit 2140. The electrical circuits of the CFM module 2200 may be connected to ground (e.g., earth) via the buckets and centrifuge for several reasons such as to prevent user contact with dangerous voltage if electrical insulation fails, and to limit the build-up of static electricity. When employing the bucket and/or the centrifuges as a transmitting or receiving antenna, the ground to earth may be necessary for the antenna to operate efficiently.

Computing unit 2140 may be any type of computing unit having a processor 2142, a memory 2144 and input/output devices 2146. For example, the computing unit may be a personal computer operating a WINDOWS operating system or Apple OSX operating system, a Unix system, or a tablet computer or smart phone, and configured to communicate such as wirelessly with CFM module 2200.

Figure 21:
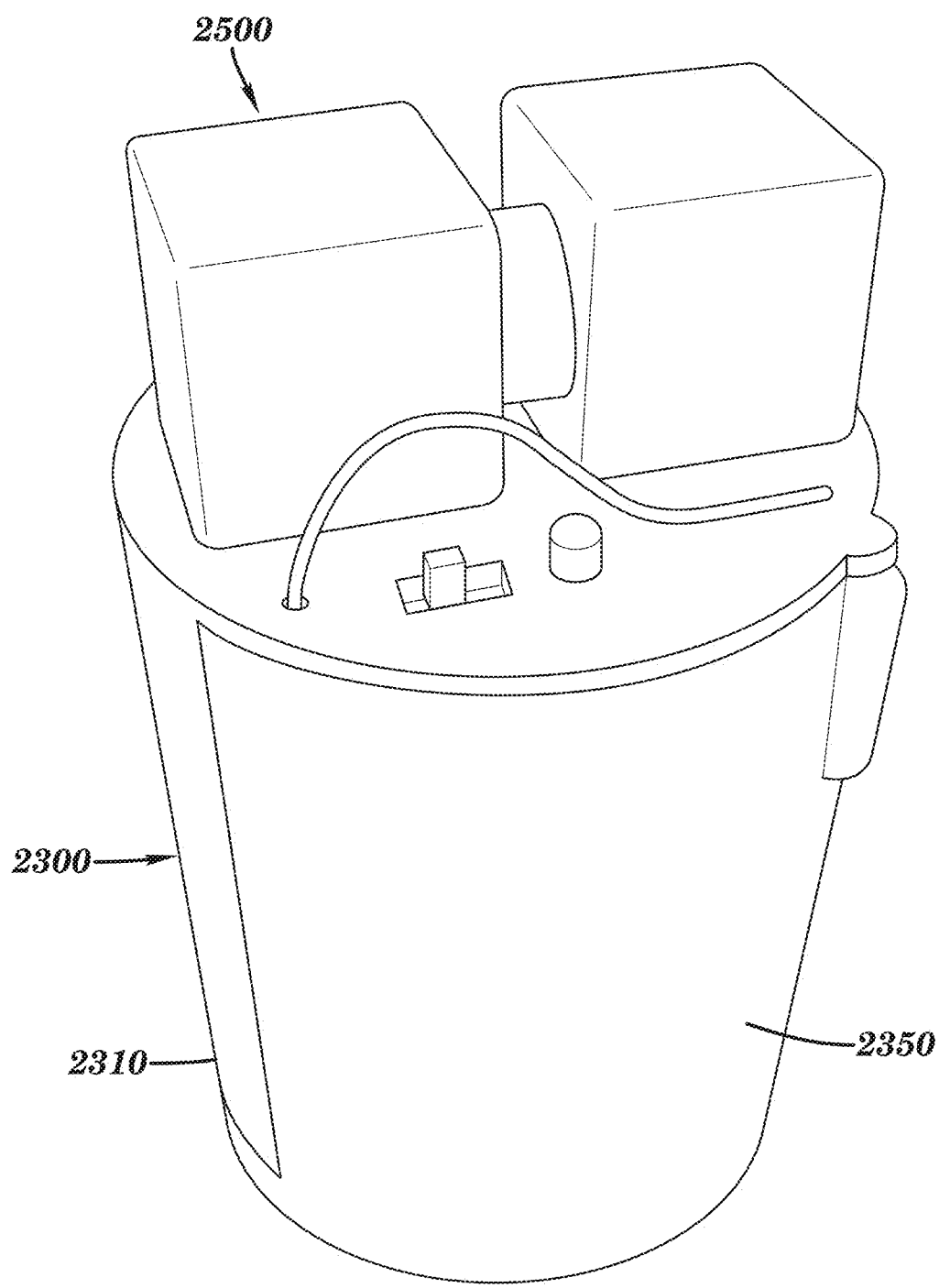
FIG. 21 is an enlarged perspective view of the centrifuge force microscope module of FIG. 18 removed from the bucket.
Figure 22:
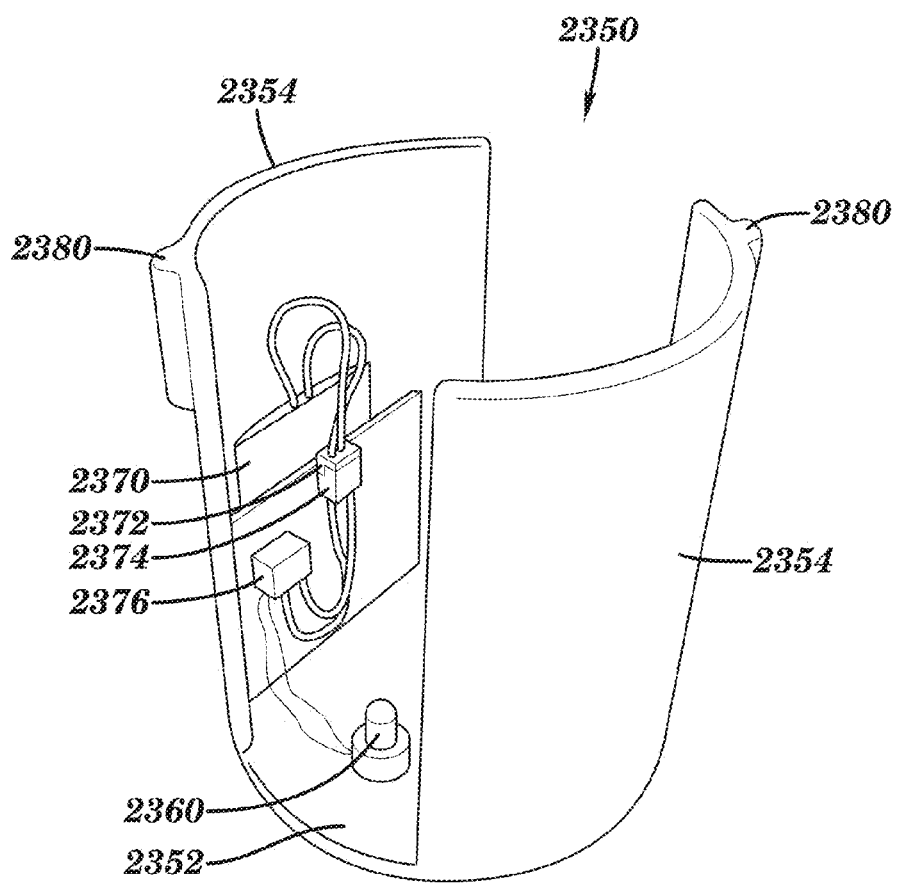
FIG. 22 is a perspective view of the lower housing of the electronics module of the centrifuge force microscope module of FIG. 21.
Figure 23:
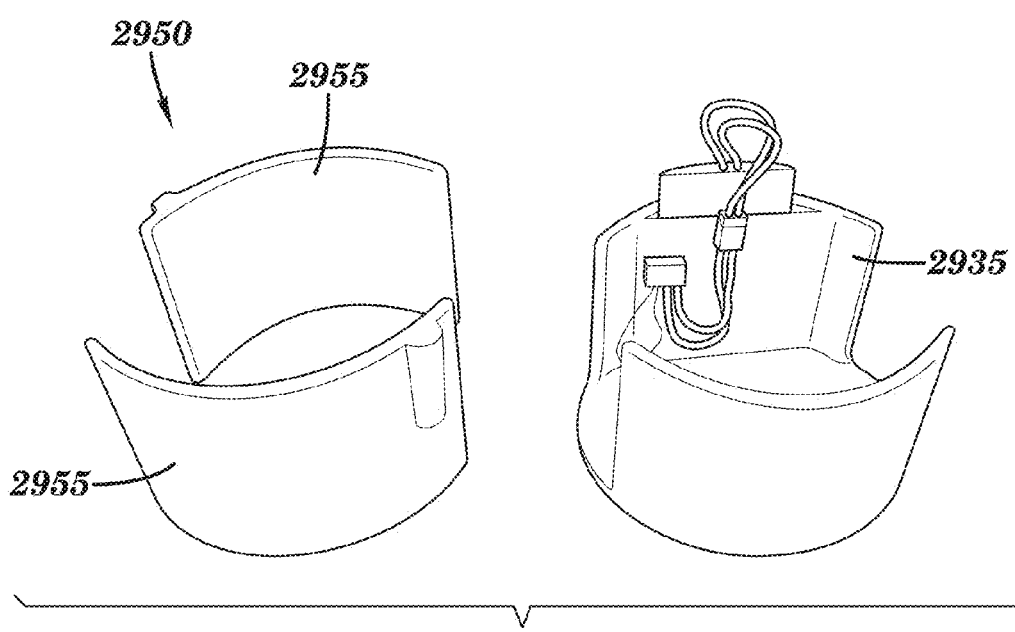
FIG. 23 is a perspective view of another embodiment of a lower housing of the electronics module of a centrifuge force microscope module in accordance with aspects of the present disclosure.
Figure 24:
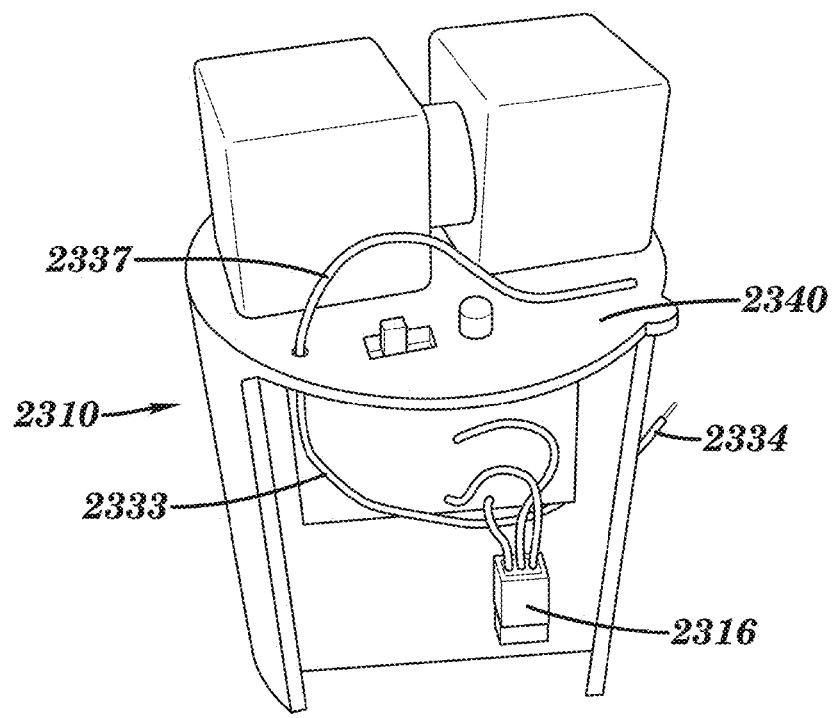
FIG. 24 is a front perspective view of the upper housing of the electronics module and the optical module of the centrifuge force microscope module of FIG. 21.

As shown in FIG. 21, electronics module 2300 may include an upper housing 2310 and a lower housing 2350. Electronics module 2300 functions as a support structure for optical assembly module 2500. In addition, electronics module 2300 may also function as a support structure and accommodate various other components. For example, as shown in FIG. 22, lower housing 2350 may include a base 2352 and upwardly extending sides 2354. Lower housing may include a light source 2360 such as a light emitting diode that faces upwardly for illuminating the sample as disclosed below. Lower housing 2350 may also include a cavity for receiving a power source 2370. For example, the power source may be a battery such as 3.3 volt lithium polymer battery. Power source 2370 may include a plug 2372 that plugs into a connector 2374 on lower housing 2350. It will be appreciated that instead of a battery, other alternative power sources may be employed. For example, power may be supplied from an ultracapacitor or a fuel cell. The lower housing of the CFM module may be readily removable allowing easy and ready removal of a discharged battery such as after conducting one or more sample experiments and readily replaced with a fully charged battery for further experiments. Connector 2374 may be connectable to a connector 2376 which is connectable to the upper housing, and when connected operable to power light source 2360. The battery maybe wired to step up converter(s) that output 5 volts so that the battery is operable to, for example, supply power to the light source in the lower housing, and as described further below, supply power to a detector such as a camera in the optical assembly module, and a single board computer in the upper housing. The upper and lower housings may releaseably interlock together, as well as forming a releaseable electrical connection between the upper and lower housing via electrical connector 2376 and electrical connector 2316 (FIG. 24). The upper housing may include outwardly extending tabs 2380 which are receivable in corresponding cavities in the bucket for fixedly restraining and inhibiting rotation of the housing in the bucket. The spaced apart side of the lower housing may allow for access to the sample as described below. As shown in FIG. 23, a lower housing 2950 may further include a separable base 2935 and a pair of side portions 2955.

Figure 25:
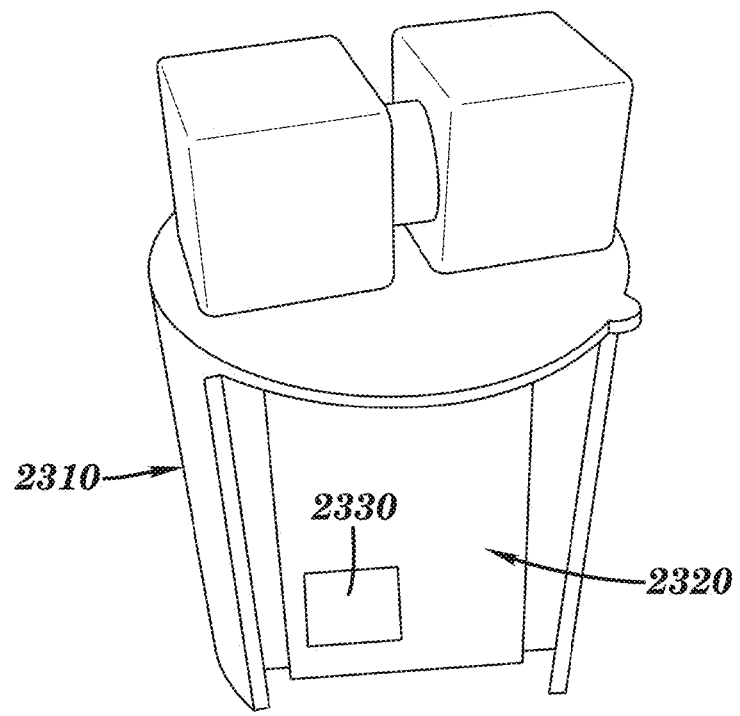
FIG. 25 is a rear perspective view of the upper housing of the electronics module and the optical module of the centrifuge force microscope module of FIG. 21.

With reference to FIGS. 24 and 25, the upper housing generally includes two parallel flat panels for supporting the electronics in the housing, and which panels are spaced apart to receive the optical assembly module therebetween. Upper housing 2310 may include plug 2316 which is alignable with and electrically connectable with connector 2376 (FIG. 22) when the upper housing is attached to the lower housing. In some embodiments, when the electrical connection is made from the interlocking pieces, the CFM module is turned on turn. The upper housing may also include a processor, microprocessor, or single board computer 2320 (FIG. 31) disposed behind circuit board 2325 and a WiFi adapter 2330 (FIG. 25). The single board computer may be an Odroid U3 single-board computer. As shown in FIG. 24, a first wire 2333 may be attached at one end to the WiFi adapter and have an exposed end 2334 disposed adjacent to the outer side surface of upper housing 2310. Exposed end 2334 of wire 2333 results in bucket 2130 and/or centrifuge 2110 acting as an antenna for communicating with computing unit 2140 (FIG. 20). It will be appreciated that wire 2333 may be connected to a resilient conducting terminal disposed along the side of the upper housing which resilient conducting terminal may contact the inside surface of the bucket when the CFM module is disposed in the bucket. A wire 2337 disposed above a top surface 2340 of upper housing 2310 may act as an antenna for communicating with computing unit 2140 (FIG. 20). When both wires 2333 and 2337 are employed the bucket and/or centrifuge may act a primary antenna and wire 2337 may act as a secondary antenna.

Figure 26:
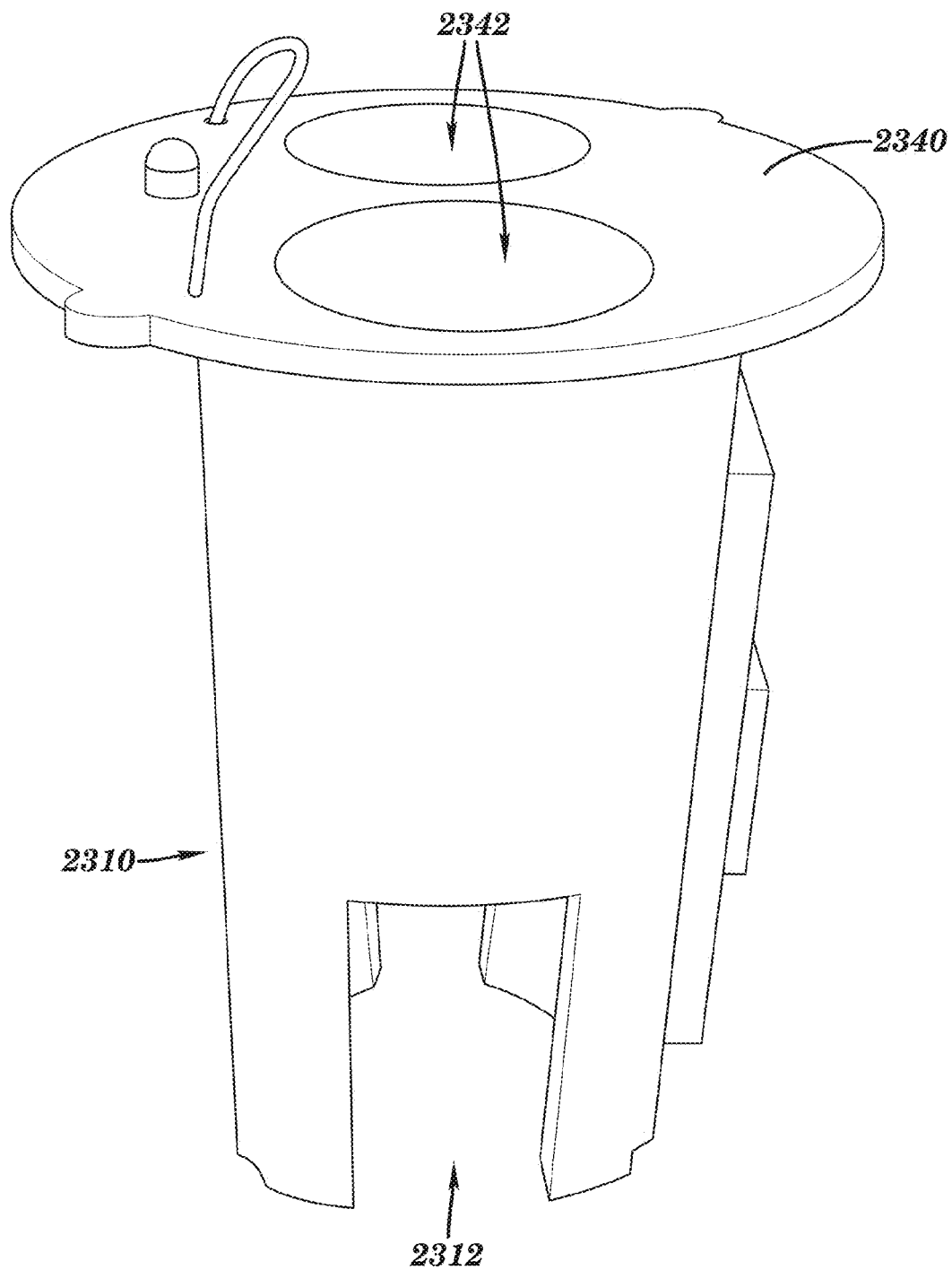
FIG. 26 is a right side perspective view of the upper housing of the electronics module of the centrifuge force microscope module of FIG. 21.
Figure 27:
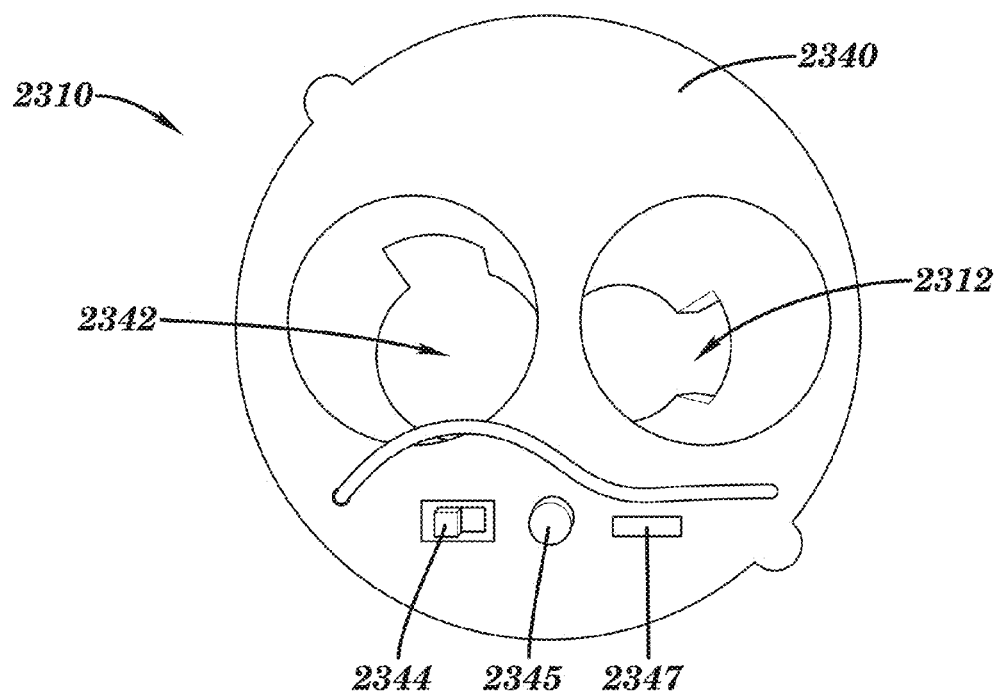
FIG. 27 is a top view of the upper housing of the electronics module of the centrifuge force microscope module of FIG. 21.

FIGS. 26 and 27 further illustrate upper housing 2310. For example, upper housing 2310 may have top surface 2340 refining a pair of passageways 2342 for receiving the optical module. An on/off button 2344 and a power indicator light 2345 maybe located on top surface 2340. The indicator light may be wired to the 5 volt USB connector of the single board computer. A charging port 2347 may be provided on the upper housing to providing a connection wired between the battery and step up converter. Upper housing 2310 may have a side opening 2312 which allows access with a side opening of the optical module for accessing the sample.

Figure 28:
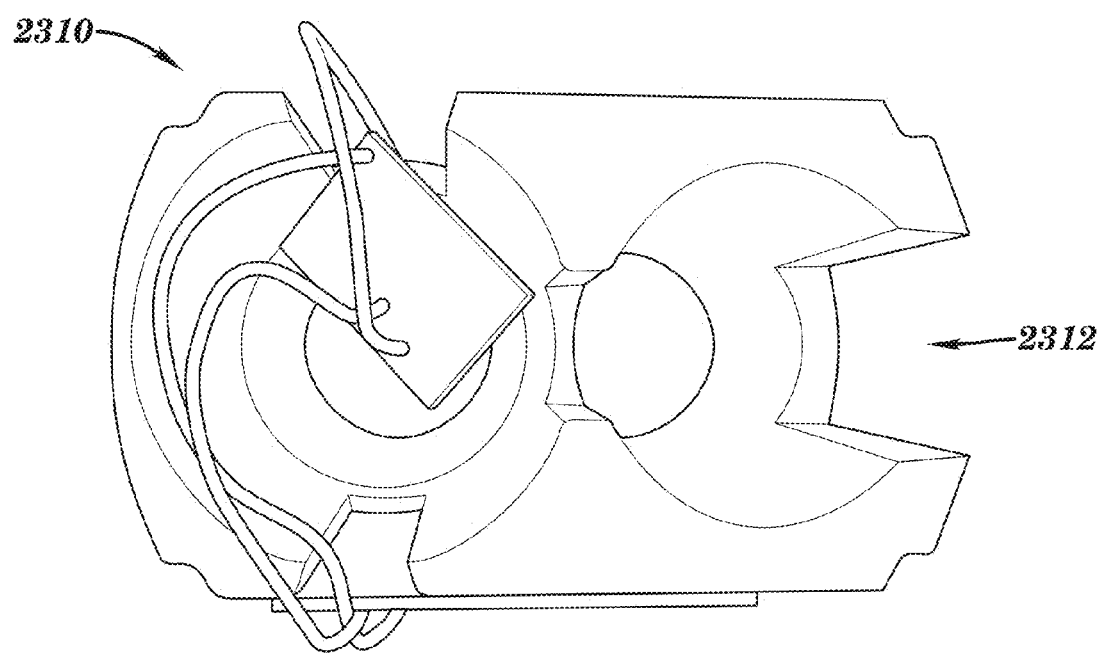
FIG. 28 is a bottom view of the upper housing of the electronics module of the centrifuge force microscope module of FIG. 21.
Figures 29, 30:
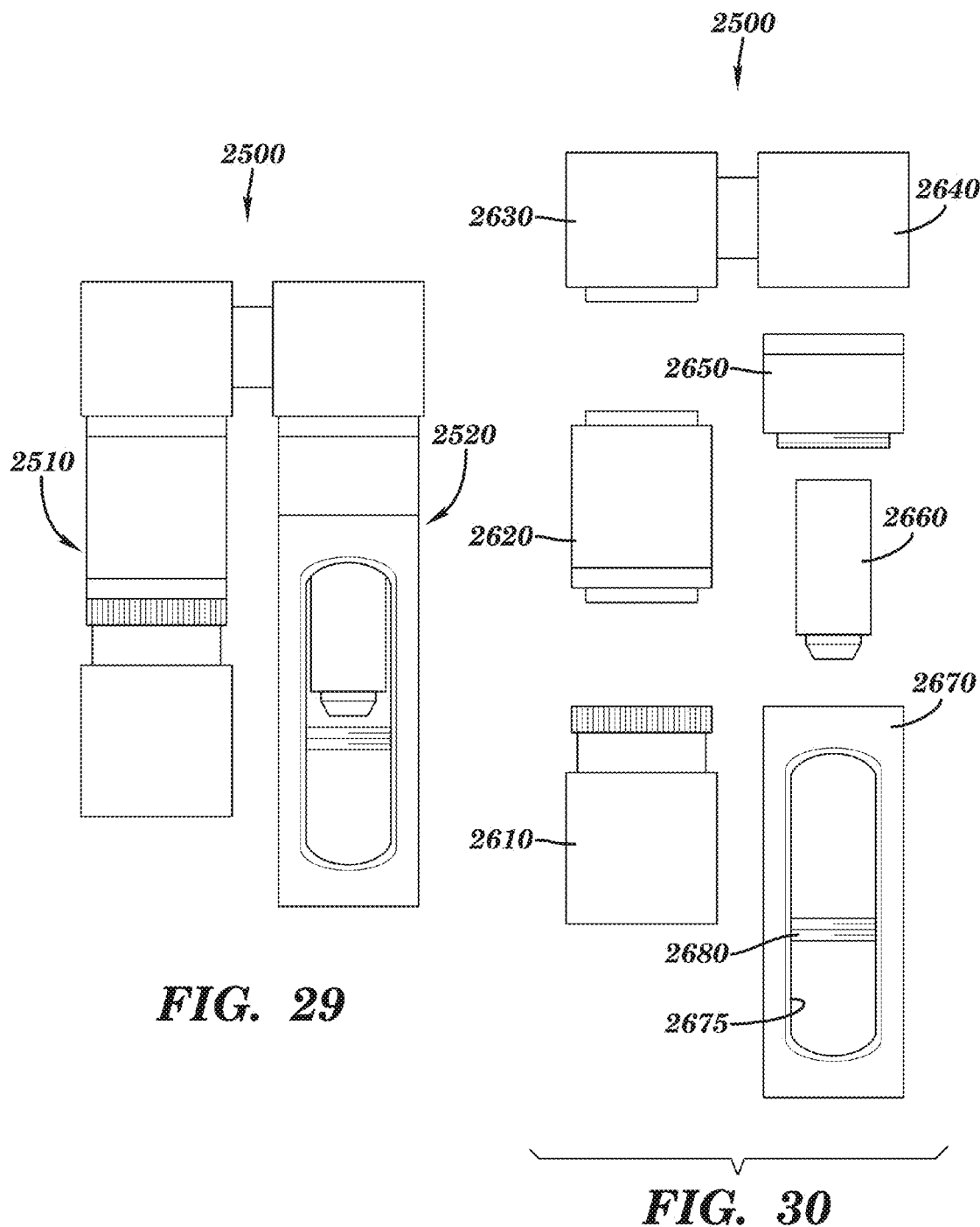
FIG. 29 is an elevational view of the optical module of the centrifuge force microscope module of FIG. 21.
FIG. 30 is an enlarged, exploded elevational view of the optical module of FIG. 29.

With reference to FIG. 28, the upper housing includes an electrical connection for electrically connecting to the detector of the optical assembly module. For example, an electrical connection may be provided for operably connecting the detector such as a camera to the single board computer disposed in the upper housing and allowing 2-way communication therebetween. The single board computer may be additionally connected to a WiFi adapter, allowing communication between the single board computer and computing unit 2140. As shown in FIG. 28, a USB MicroB plug breakout board 2349 may be disposed at the lower end of one of upper housing portion 2310 for connecting to a USB port on detector 2610 (FIG. 29). The connection operably carries power to the detector and data signals to the single board computer disposed in the upper housing.

As shown in FIG. 29, optical module 2500 may generally include the major components of a microscope. For example, in this illustrated embodiment, optical module 2500 may include a generally inverted U-shaped optical assembly module comprising a first leg 2510 and a spaced-apart second leg 2520. As best shown in FIG. 30, optical module 2500 may include a detector 2610 such as a digital imager or camera, a tube 2620, a first 45-degree turning mirror 2630, a second 45-degree turning mirror 2640, a tube lens 2650, a lens or an objective 2660, a support 2670, and a sample support 2680. The sample support of sample may be accessible through a side opening 2675 which is alignable by rotating support 2670 with side opening 2312 (FIGS. 26-28) in the upper housing.

The 45-degree turning mirror may be disposed at the base of the legs of the optical module to redirect the light paths to accommodate a longer path length. The optical module may additionally include illumination components such as diffusers, lenses, and apertures including pinholes, translation stage for focusing the sample, and/or relay lenses. As noted above, support 2670 may be disposed with opening 2675 positioned to the side for access to the sample when the CFM module is assembled. Other embodiments of an optical module may include a light source. For example, a light source may be operable attached to a support below the sample. To house the optics, commercially available lens tubes and components by Thorlabs may be employed. To reduce weight, the housing from the objective lens may be removed, and instead use a custom threaded adapter to mate the objective threads with the standard lens tube threads. An open lens tube for support 2670 may be used so that the sample chamber can be more readily interchanged. In operation of the sampling system, the optical module comprises an optical axis disposed substantially perpendicular to an axis of the centrifuge.

Figure 31:
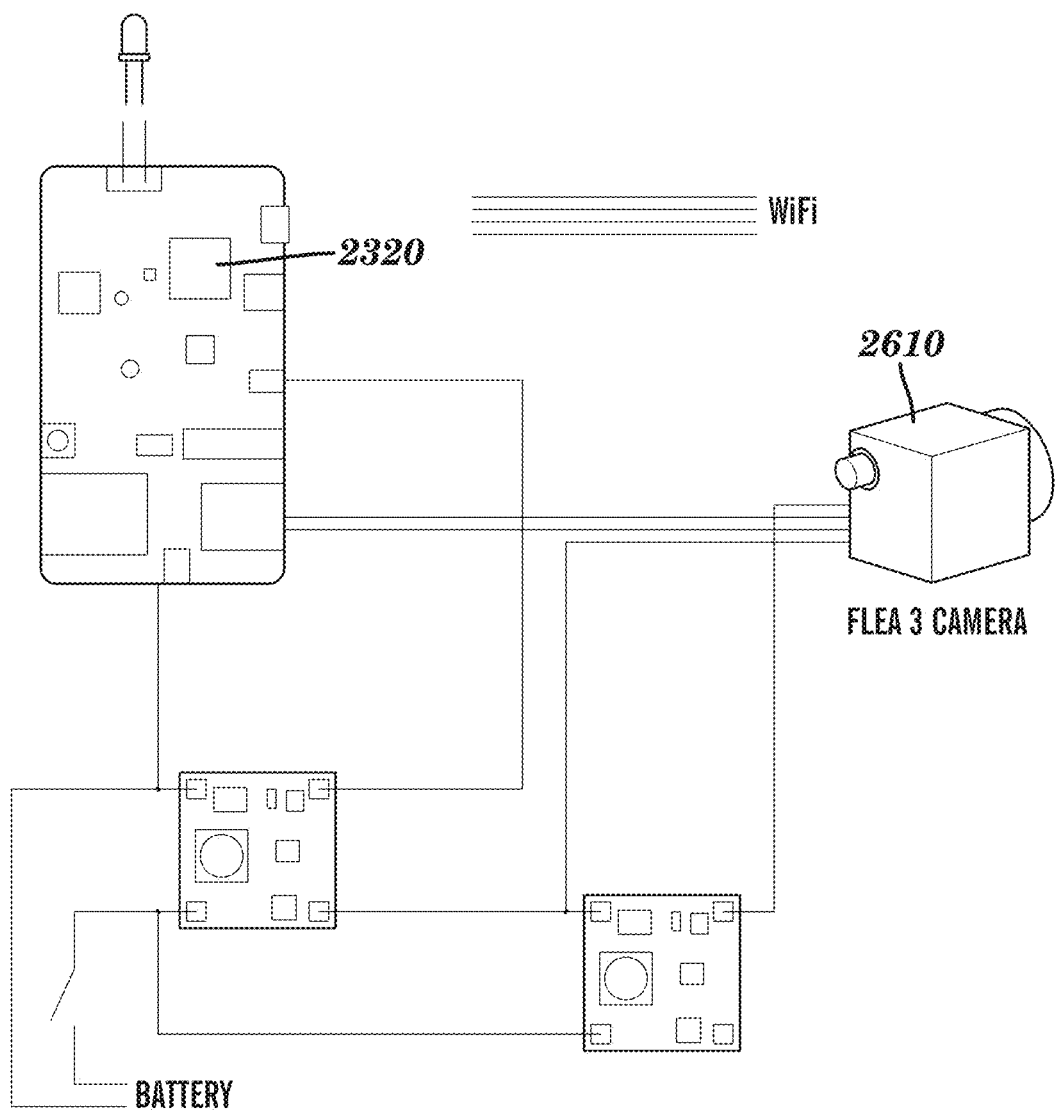
FIG. 31 diagrammatically illustrates the electrical system of the electronics module of the force microscope module of FIG. 21.

FIG. 31 diagrammatically illustrates the electrical systems of the electronics module which is operably connected to detector 2610 of the optical module. The electrical system may provide two functions, i) to provide power to the electrical components, and ii) to facilitate communication and data transfer (and possibly data processing) from the detector to a storage device or external computer.

Figure 32:
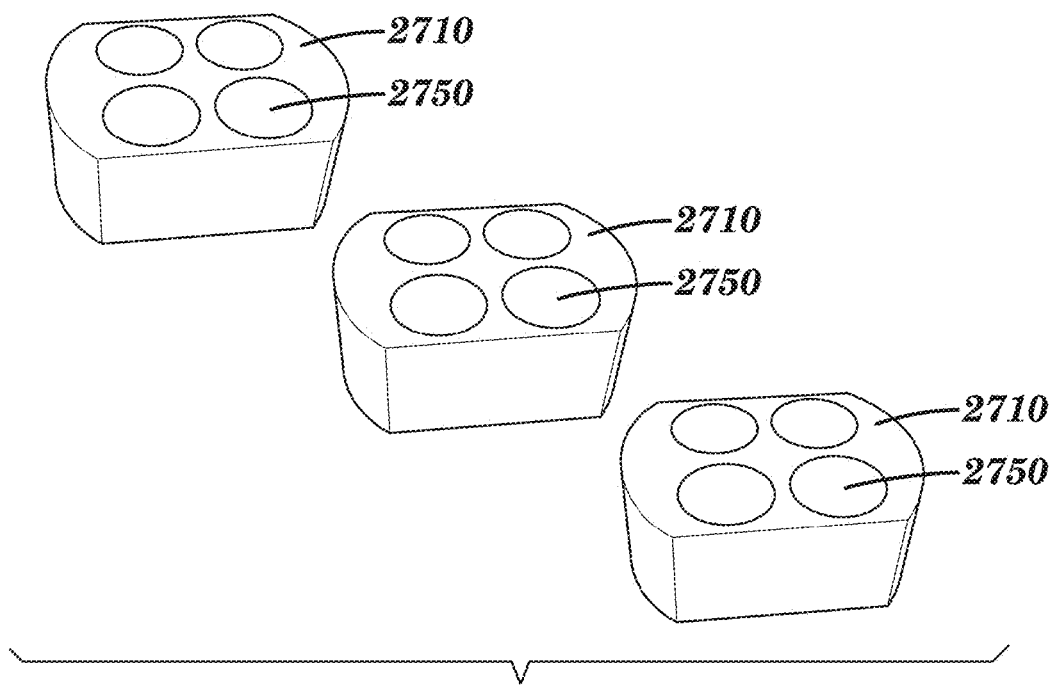
FIG. 32 is an exploded perspective view of the counterweight module of FIG. 19.
Figure 33:
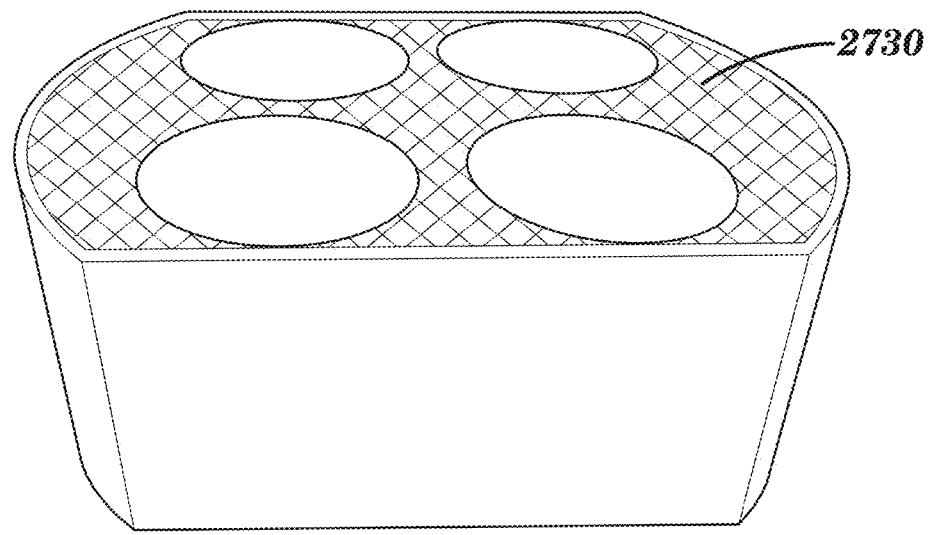
FIG. 33 is a perspective view of an embodiment of a counterweight holder in accordance with aspects of the present disclosure for a counterweight module.

With reference to FIGS. 32 and 33, a counterweight module 2700 may include a plurality of holders 2710 and removable weights 2750. Simply placing the same weight in the opposing bucket that corresponds to the CFM module is not sufficient to counterbalance the system. For example, three holders may be employed and allow an operator to adjustably take into account the weight distribution along the height of the bucket. The design of the holder may employ small stackable weights that are placed in four spaced apart receptacles in each of three vertically stacked housings. The weights may be small metal discs, washers, or coins. For example, an operator can first weigh the CFM module and then determine the correct number of weights to match the CFM module. Next, the operator can distribute the weights within the twelve compartments in the holders to match the center of mass in all three dimensions. It has been observed that distribution of the weights in the vertical dimension (i.e. along the height of the bucket) has a greater effect compared to distribution of the weight laterally or horizontally. Such a counterweight module avoids the likelihood of damaging various components of the CFM module and centrifuge without proper counterbalancing. As shown in FIG. 33, the holder may be fabricated from a plastic material and be generally hollow and having a plurality of reinforcing ribs 2730. From the present description, other counterweight modules may include a holder having a one or more weights and one or more mechanical actuators or small motors to move the weight as needed to meet the weight distribution.

In other embodiments, a plurality of the CFM modules may be employed in multiple buckets. In still other embodiments, wireless communication may be provided between at least two CFM modules disposed in two buckets.

The optical module may provide fixed or adjustable dimensions between the various components so that focused images are obtainable. In other embodiments, instead of the detector, imager, or camera being a part of the optical module, the detector, imager, or camera may be part of the electronics module. For example, the detector, imager, or camera may be attached to a lower housing of the electronics module. The various components between the electronics module and the optical module may provide focused images when the electronics module and optical module are assembled. In addition, the components may be adjustable and testable for focusing the images o the sample, for example prior to installing the CFM module in a bucket for testing. While a two piece housing of the electronic module is generally disclosed, it will be appreciated that the housing may include more than two releaseably connectable pieces. Data from the CFM module may be wirelessly transmitted from the CFM module or stored in memory, which memory may be removable or downloadable.

In other aspects of the present disclosure, computing unit 2140 (FIG. 20) may acts as an interface to set up and control the experiments, and then to retrieve and analyze the data. In the absence of the computing unit or an external computer, the onboard CFM processor 2320 (FIG. 31) or a computer controlling the centrifuge itself could control the system. Operable software may be provided in connection with control of the CFM module and centrifuge, and the transfer and analysis of data resulting from experiments using the CFM module.

Figure 34:
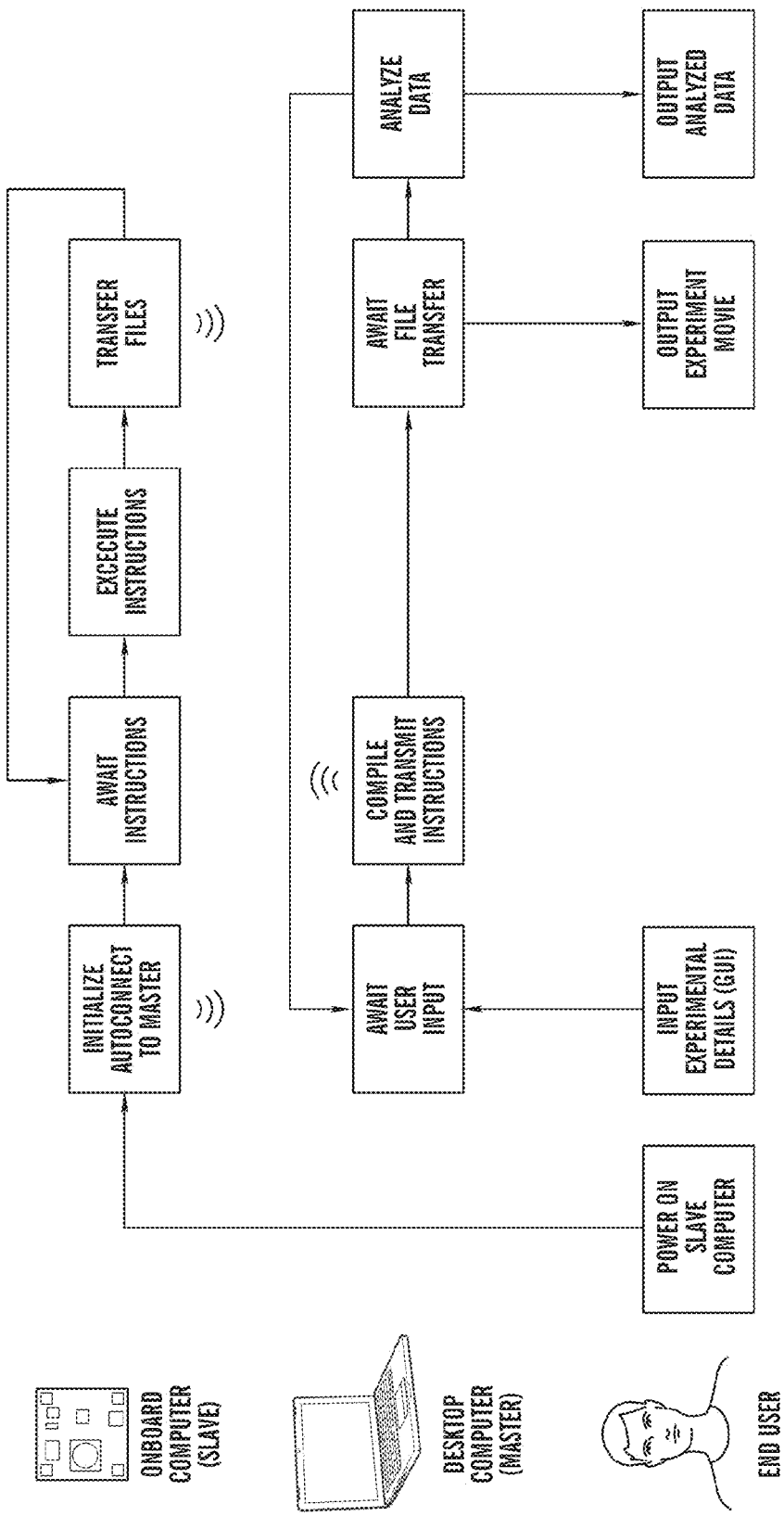
FIG. 34 is a flowchart of one embodiment of a method for operating the centrifuge force microscope module of FIG. 17 in accordance with aspects of the present disclosure.

FIG. 34 illustrates an embodiment of a method for operating centrifuge force microscope system 2100 (FIG. 20) in accordance with aspects of the present disclosure. For example, operable software residing on the computing unit 2140 (FIG. 20) such as a desktop computer and onboard processor 2320 (FIG. 31) of CFM module 2200 (FIG. 20) may automate the initialization of the CFM module, the collecting of data, and the transfer of data to an external device. When the CFM module is turned on via the on/off switch, power is given to the onboard computer and the boot sequence commences. Through software, the computer automatically generates a WiFi hotspot which can be recognized by any local WiFi connected computer. A command is then run from the external computer to establish a connection, and send relevant experimental instructions to the onboard computer (e.g. number of camera frames to collect, where to store files, frame rate and resolution, etc.) which then executes those instructions and starts the experiment. Upon completion of an experiment, files may be automatically sent by WiFi to the external computer. In other embodiments, the software may automatically perform the start up sequences when the on/off switch is turned to on, and may include booting the onboard computer, powering the camera, powering the light source, running scripts on the onboard computer, communicating with the camera, and communicating with the centrifuge. An indicator light may be wired to provide visual feedback on the status of the equipment including indicating when power is available and indicating when the system is ready to go.

Figure 35:
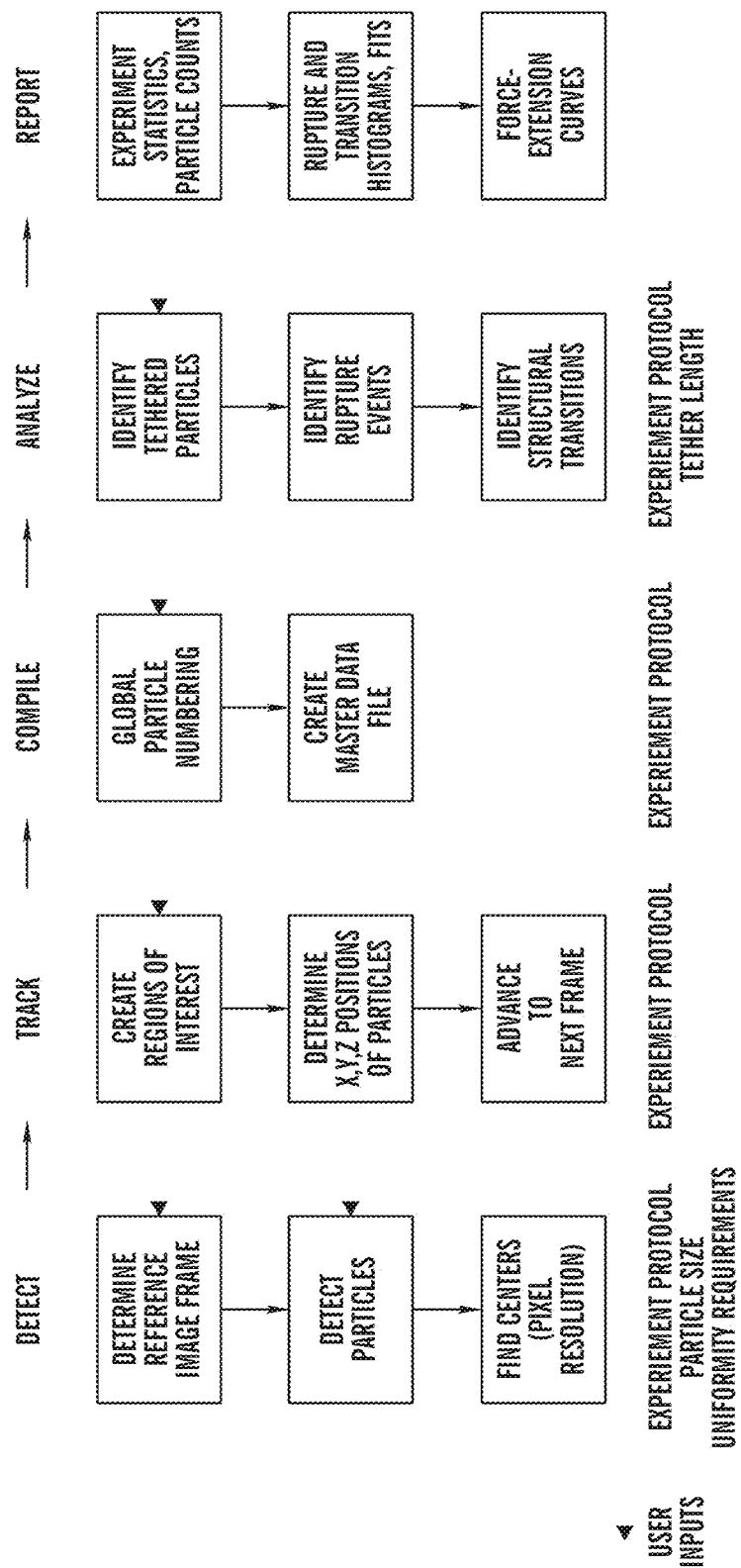
FIG. 35 is a flowchart of one embodiment of a method for analyzing data obtained in connection with operation of the centrifuge force microscope module of FIG. 17 in accordance with aspects of the present disclosure.

As shown in FIG. 35, analysis of data may include a user observing an image frame of the beginning of the experiment, and providing inputs regarding particles to track. The operable software may be designed to analyze the tracked particles during the experiment.

It may be desirable to have computer control of the centrifuge for a more integrated user experience. Since most centrifuges do not have this feature, one option may be to use an upgraded mainboard from the manufacturer that enables computer control. Another option may be to install a small computer on the inside of the front panel to generate computerized "keypad" signals, overriding the front panel of the instrument and allowing computer control. The computer control of the centrifuge may be interfaced with both the external computer, e.g., computing unit 2140 (FIG. 20) and the onboard processor or computer 2320 (FIG. 31) of the CFM module.

In light of the present description, it will be appreciated that the techniques and aspects of the present disclosure provides a system that may enable user-friendly, high-throughput single molecule experiments using only common bench top centrifuges that exist in laboratories worldwide. Such systems may expand the functionality of centrifugation to provide real-time microscopy of samples as centrifugal forces are applied. The system may allow single-molecule experiments by researchers in single-molecule analysis, as well as by a broad range of non-specialist researchers in other fields.

It will be further appreciated that the techniques and aspects of the present disclosure allow for measuring properties of biomolecules for basic research or drug discovery, with the ability to monitor an individual molecule. Such single molecule experiments may generate information for measuring or screening biomolecular interactions and probing structure of individual molecules such as proteins and nucleic acids. Some of the information from single-molecule experiments cannot be determined from typical ensemble "test tube" measurements, which report only the "average" of the population. The techniques and aspects of the present disclosure may reduce the cost compared to single molecule instruments, allow for a higher throughput by running more than one sample at a time with concurrent data collection, and allow operators to readily and easily maintain the system, conduct the experiments, and analyze the data.

4 Applications

Using the centrifugal force (and possibly other forces) of a spinning sample, spinning force system 100 is capable of performing single-molecule experiments for application in a wide range of areas, including receptor-ligand interactions, DNA mechanics, the kinetics of motor proteins, and the dynamics of intramolecular transitions such as protein folding and unfolding. In addition, spinning force system 100 can also be used for high-throughput molecular screening in which thousands of single-molecule experiments of the same or different types can be performed in parallel and/or in series. This can be particularly useful for drug discovery and screening. The following section provides several scenarios in which spinning force system 100 is useful.

4.1 Example I

One application of spinning force system 100 relates to studying the molecular interactions between two or more interacting molecules or molecular complexes, including, for example, measuring the association rate $K_{on}$ and dissociation rate $K_{off}$ of the interaction, identifying metastable states, and determining the transition rates between such states. Examples of interacting molecules suitable as subject of study include receptor-ligand pairs, such as biotin-streptavidin, antibody-antigen, enzyme-substrate, and DNA-polymerase.

Referring to FIGS. 5A-5D, one procedure of preparing a sample containing two interacting molecules A (e.g., biotin) and B (e.g., streptavidin) for measurement is illustrated.

Figure 5B:
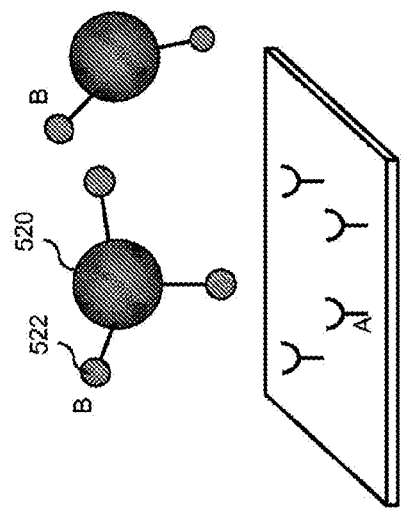
FIGS. 5A-5D are schematic representations of a procedure for preparing a sample to be measured by the spinning force system of FIG. 1.
Figure 5D:
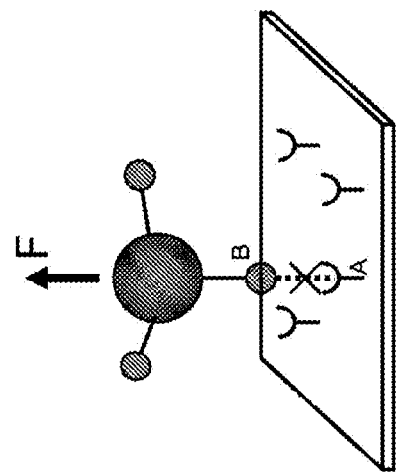
Figure 5A:
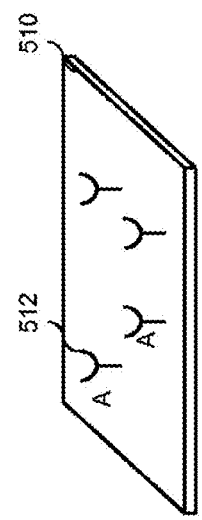

For example, in FIG. 5A, a cover glass 510 is coated with a dispersed layer of molecule A 512 using proper functionalization techniques such as physisorption or covalent linkage.

In FIG. 5B, a solution of glass beads 520 is then added onto cover glass 510. Each bead is pre-coated with one or more molecules B 522, again using proper functionalization techniques.

Figure 5C:
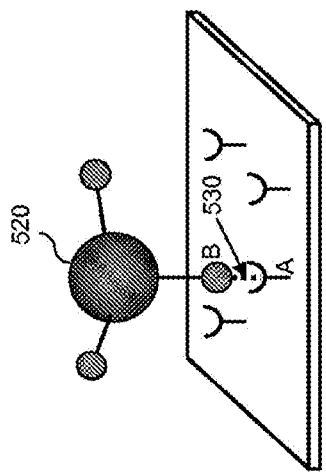

In FIG. 5C, cover glass 510 is incubated with glass beads 520 to enable formation of interaction 530 between molecules A and B. Consequently, some beads 520 become attached to the surface of cover glass 510 through newly formed interactions 530. Unattached beads can be removed from the surface by rinsing with an inactive solution, or alternatively, removed by a centrifugal force applied during measurement. In some examples, the amount of interactions 530 formed during the incubation can be controlled, for example, by the temperature and time duration of the incubation, the concentration of pre-coated bead solution, and the density of molecule A 512 seeded on cover glass 510.

In FIG. 5D, once the sample is ready for measurement, it is loaded onto spinning force system 100. In this example, cover glass 510 is configured to be parallel to rotational axis 102 of system 100. The rotation of the sample therefore results in a centrifugal force F on bead 520, pulling it away in a direction perpendicular to the surface of cover glass 510. The movement of bead 520 can be monitored using one or more of the imaging techniques described above. When the magnitude of centrifugal force F is sufficiently high to rupture interaction 530, bead 520 is released from cover glass 510.

In this example, hundreds or thousands of molecular interactions 530 can be formed and observed in one experiment, allowing statistical analysis of such observations to be performed in a highly efficient manner.

4.2 Example II

Another application of spinning force system 100 relates to studying the intramolecular dynamics of a single molecule or a molecular tether (e.g., a protein or a DNA tether), including, for example, measuring the folding, unfolding, stretching, and relaxation of a molecular strand.

FIGS. 6A-6D illustrate use of system 100 in a procedure for preparing a sample containing a molecular tether to be measured.

In FIG. 6A, a cover glass 610 is coated with a dispersed layer of molecule A 612 using proper functionalization techniques such as physisorption.

In FIG. 6B, a solution of glass beads 620 and a solution of molecular tethers 630 (e.g., DNA tethers as shown in FIGS. 6B-6D for illustrative purposes) are added onto cover glass 610. Each bead 620 is pre-coated with one or more molecule A 612, and each molecular tether 630 is functionalized with one or more molecule B 632 capable of forming interactions with molecule A 612. Examples of commonly used functionalization techniques and procedures include silanization for glass substrate, formation of a peptide bond between a carboxylated surface and a free amine on a protein, and formation of disulfide bonds or S—C bonds for cysteine residues.

In FIG. 6C, cover glass 610 is incubated with glass beads 620 and molecular tether 630 to enable formation of interaction 640 between molecules A and B. Consequently, some beads 620 become attached to the surface of cover glass 610 through a newly formed interaction 640 between bead 620 and molecular tether 630 and another newly formed interaction 640' between molecular tether 630 and cover glass 610. Unattached beads can be removed from the surface by rinsing with an inactive solution, or alternatively, removed by a centrifugal force during measurement. In some examples, the amount of interactions 640 formed during incubation can be controlled, for example, by the temperature and time duration of incubation, the concentration of pre-coated bead solution and molecular tether solution, and the density of molecule A 612 seeded on cover glass 610.

In FIG. 6D, once the sample is ready for measurement, it is loaded onto spinning force system 100. For illustrative purposes, cover glass 610 is configured to be parallel to rotational axis 102 of system 100. The rotation of the sample therefore results in a centrifugal force F on bead 620, pulling it away in a direction perpendicular to the surface of cover glass 610. The movement of bead 620 indicates the force-induced conformational changes of molecular tether 630 and can be used to measure variables characterizing the folding, unfolding, stretching and relaxation of the molecular tether in response to an external force. When the magnitude of F is varied (without exceeding the bond rupture force to break interaction 634), the force dependent dynamics of DNAs can also be quantified.

Again, in this example, hundreds or thousands of molecular tethers 630 can be studied in a single experiment, allowing statistical analysis of the results to be performed efficiently.

4.3 Example III

Another application of spinning force system 100 relates to studying the characteristics of molecules or molecular interactions in controlled chemical environments, including, for example, quantifying molecular dynamics at various temperatures, pH conditions, and/or salt concentrations, as well as in the presence of various kinds of surfactants and/or enzymes.

FIGS. 7A-7D illustrate use of system 100 in a procedure for preparing a sample containing a molecular tether 730 that can be modified by a restriction enzyme 760.

Figure 7B:
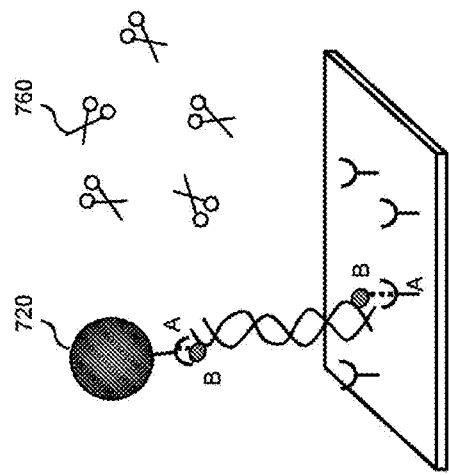
FIGS. 7A-7D are schematic representations of a further procedure for preparing a sample to be measured by the spinning force system of FIG. 1.
Figure 7D:
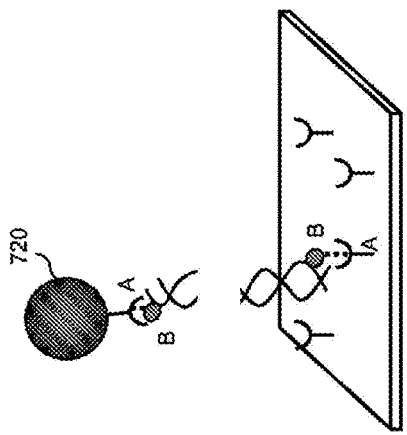
Figure 7A:
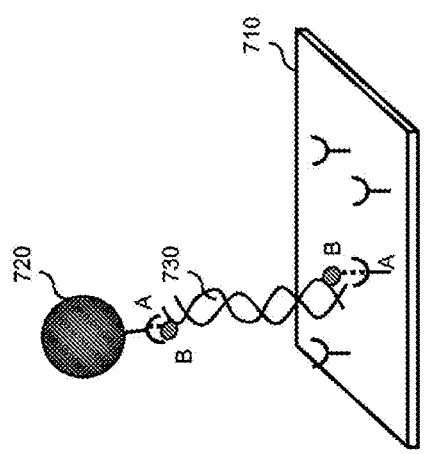

For example, in FIG. 7A, molecular tether 730 (e.g., a DNA strand) is attached to a cover glass 710 and a particle 720 using preparation techniques described above with reference to FIGS. 6A-6C.

In FIG. 7B, a solution of restriction enzymes 760 is added onto cover glass 710. Examples of restriction enzyme 760 include an enzyme that cuts double-stranded or single-stranded DNA at specific recognition nucleotide sequences (known as restriction sites). Restriction enzymes can be used for manipulating DNA in various applications such as DNA digestion and gene insertion.

Figure 7C:
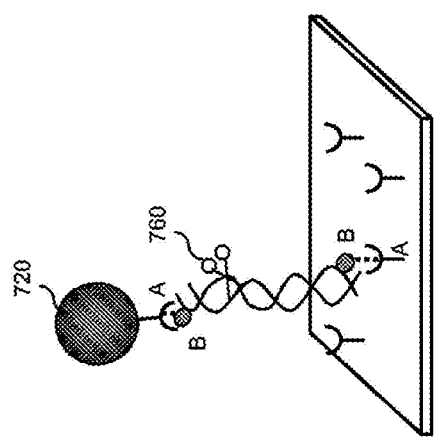

In FIG. 7C, molecular tether 730 is incubated in the solution of restriction enzymes 760 to allow one or more enzyme molecules to bind to the restriction sites of tether 730.

In FIG. 7D, upon binding with tether 730, restriction enzyme 760 makes incisions at selected locations in tether 730, cutting the tether into two or more disconnected pieces. As a result, particle 720 is released from the surface of cover glass 710. Particle release can be observed using the imaging techniques described above.

Some or all of the procedures shown in FIG. 7A-7D may be performed during spinning. For example, the binding/interaction between tether 730 and restriction enzyme 760 may be monitored under the influence of a controlled centrifugal force applied to particle 720 as shown in FIG. 6D.

4.4 Example IV

Referring to FIGS. 11A-11D, in a specific example, spinning force system 100 is used to perform massively parallel single-molecule experiments for the characterization of the force-dependent unbinding kinetics of an antibody-antigen interaction.

Referring to FIG. 11A, a cover glass 1110 is coated with a dispersed layer of digoxigenin (molecule A 1112). Functionalized cover glass 1110 was prepared by base washing a glass coverslip (immersed for 5 minutes in a boiling solution of 1 part 30% $H_2O_2$, 4 parts $NH_4OH$, and 19 parts d-$H_2O$), followed by adsorption of monoclonal anti-digoxigenin (11094400, mouse monoclonal, available from Roche, Boulder, Colo.). The cover glass was then washed with a blocking buffer composed of phosphate buffered saline with 0.1% Tween 20 and 1 mg/mL dephosphorylated alpha-casein (C8032, Sigma Aldrich, St. Louis, Mo.). The experiments described below were performed in the same blocking buffer to decrease non-specific adhesion of beads to the surface of cover glass 1110.

In FIG. 11B, digoxigenin (molecule B 1132) was tethered to glass beads 1120 with a diameter of 2.8 microns by molecular tethers, e.g., DNA tethers 1130. Monoclonal anti-digoxigenin (molecule A 1112) is capable of forming a bond with digoxigenin (molecule B 1132). More specifically, diogoxigenin labeled DNA was prepared by labeling the cohesive ends of 48 kB lambda phage DNA (N3013S, available from New England Biolabs, Ipswich, Mass.) with biotin (biotin-14-dATP and biotin-14-dCPT, available from Invitrogen) using Klenow polymerase (M0212S, available from New England Biolabs), follows by purification using, for instance, QiaQuick purification kit available from Qiagen (Valencia, Calif.). The biotinylated DNA was then cut in half with the XbaI restriction enzyme (R014SS, New England Biolabs) and re-purified. The overhanging ends of the resulting 24 kB DNA were filled in and labeled with a single digoxigenin (dig-11-dUTP, available from Roche) or plain nucleotides for dig-labeled or unlabeled DNA. Finally, the DNA was re-purified and the dig-DNA was mixed with unlabeled DNA in a 1:4 ratio. The mixture of dig-DNA and unlabeled DNA was reacted with streptavidin labeled beads (Dynabeads M-270, available from Invitrogen, Carlsbad, Calif.) for use in the experiment.

In FIG. 11C, cover glass 1110 is incubated with a solution of the DNA-functionalized glass beads 1120 to enable the formation of bonds between molecules A and B. Consequently, some beads 1120 (e.g., beads 1 and 2) become attached to the surface of cover glass 1110 through a newly formed bond between molecules A on cover glass 1110 and molecules B attached to beads 1 and 2. Other beads, such as bead 3, are non-specifically bound to the surface of cover glass 1110, for instance by hydrogen bonding. In some examples, the amount of bonds formed during incubation can be controlled, for example, by the temperature and time duration of incubation, the concentration of pre-coated bead solution, and the density of molecule A 1112 seeded on cover glass 1110.

In FIG. 11D, once the sample is ready for measurement, it is loaded onto spinning force system 100 and rotated at a constant velocity in order to apply a uniform force field to all of the beads in a direction perpendicular to the surface of cover glass 1110. Some singly-tethered beads (e.g., bead 1) responded by moving away from cover glass 1110 by a distance x consistent with the compliance of the double-stranded DNA tether 1130. Other singly-tethered beads (e.g., bead 2) detached from cover glass 1110 as a result of the rupture of the bond between molecules A and B. Non-specifically bound beads (e.g., bead 3) remained at or near the surface of cover glass 1110.

Figures 12A, 12B, 12C, 12D:
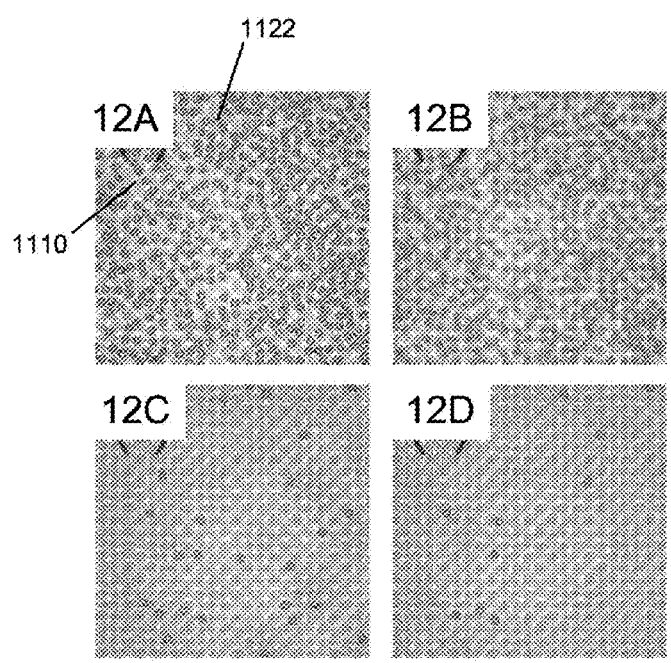
FIGS. 12A-12D are images of a spinning force experiment using the sample of FIGS. 11A-11D.

Referring to FIGS. 12A-12D, time lapse images show the progress of the bond rupture experiment illustrated in FIG. 11D. The images are obtained from videos recorded at 10 frames per second. At the start of the experiment (FIG. 12A), thousands of anti-digoxigenin functionalized beads 1122 are bound to cover glass 1110. Prior to beginning the experiment, the objective lens (150 in FIG. 1) of spinning force system 100 is focused at a distance of one tether-length (x) away from the surface of cover glass 1110 (FIG. 12B). Since all the beads are resting on the surface of the cover glass at the start of the experiment, the beads are not in the focal plane of the objective lens and thus appear blurry. When a centrifugal force is generated that pulls the beads away from cover glass 1110, beads tethered by a single DNA molecule move into focus (FIG. 12C). As single receptor-ligand bonds (i.e., digoxigenin-anti-digoxigenin bonds) rupture, beads detach from cover glass 1110, resulting in fewer visible beads over time (FIG. 12D).

Force clamps ranging from hundreds of femtoNewtons to several picoNewtons were applied using spinning force system 100. Analysis of videos of the experiment was performed by identifying locations of fully tethered beads at a frame near the beginning of the movie (once full rotational speed was reached) and analyzing small regions of interest at each location in subsequent frames to determine the time of bond rupture. Bead locations were determined by performing a background subtraction, making a binary image, and finding the center positions and the variance of a region of interest around each bead. The image variance is important because non-specifically adsorbed ("stuck") beads can be distinguished from tethered beads by their variance. Stuck beads were excluded from the analysis. The rupture time for each bead was identified by a dramatic drop in the measured variance to near zero, corresponding to a grey, bead-free image. In rare cases, where multiple drops in the variance were observed for a particular bead, that bead was excluded from analysis, as this behavior indicated the possibility of a multiple tether.

Figure 13:
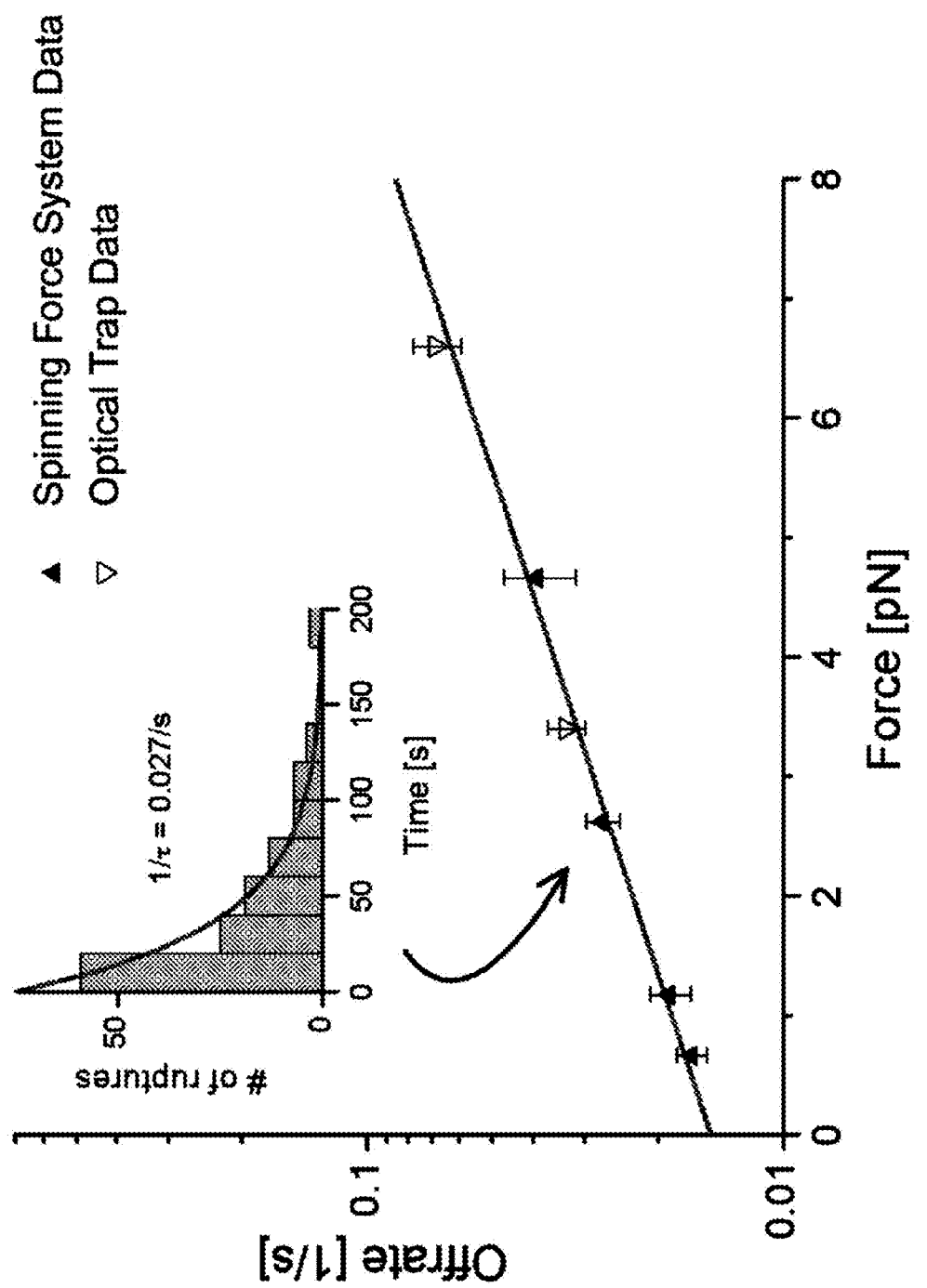
FIG. 13 is a graph of data collected during the experiment of FIGS. 12A-12D.

Referring to FIG. 13, a histogram of the bond rupture time obtained using spinning force system 100, with a 20 second bin width (10 seconds for the highest optical trap force), was fit with a decaying exponential curve with no offset. The resulting time constants and associated fitting errors were used to determine the force-dependent off-rate $k_{off}(f)=k_0 \exp(f/f_\beta)$ for the interaction of digoxigenin and its antibody using an Arrhenius approach with force-dependence modeled by a single, sharp barrier.

The force imparted on the beads by spinning force system 100 was calculated as $F=m\omega^2 R$, where $m=6.9\times10^{-12}$ g is the mass of the bead (calculated using the manufacturer's bead specifications of 2.8 mm diameter and 1.6 g/cm$^3$ density), R=385.5 mm is the distance of the bead from the axis of rotation, and w is the magnitude of the angular velocity of the system. A small additional force from the weight of the bead was included using the Pythagorean theorem. The data plotted in FIG. 13B includes data obtained using spinning force system 100 (filled triangles) and using an optical trap system (open triangles). Each spinning force system data point was obtained from a single experiment lasting a few minutes. Plotted error bars result from the uncertainty in a least squares fit to the data. A stress-free off-rate of $k_0=0.015+/-0.002$ s$^{-1}$ and a force scale of $f_\beta=4.6+/-1.3$ pN were found. These results are in good agreement with previously determined optical trap data and fall within the margin of error of previous AFM experiments.

4.5 Example V

Another application of spinning force system 100 relates to studying different types of molecular interactions and/or molecular dynamics in parallel. This application allows a direct comparison of molecular events of similar or different nature, such as the mobility of two different motor proteins, the compliance of various pieces of DNA strands, and the affinity of various receptor-ligand pairs. To distinguish the observations of motion characteristics resulted from distinct molecular events, each type of event can be uniquely labeled, for example, using fluorescent tracers or other kinds of markers. For example, in cases where two types of cytoskeletal proteins (e.g., microtubules and actin filaments) are studied at once, each type can be labeled by fluorescent beads of distinct emission wavelengths. By using selected optical filters to alternate observation of photons of different colors, the motion characteristics of each type of cytoskeletal proteins can be distinguished based on the resulting fluorescent images.

4.6 Example VI

Although the previous examples are provided primarily in the context of measuring molecular dynamics or interactions, spinning force system 100 is also useful in measuring characteristics of interactions that occur on a cellular and/or tissue level. One example is to study the adhesion strength between adherent cells (e.g., endothelial or epithelial cells) and the underlying substrate or matrix to which the cells adhere. A monolayer of adherent cells can be seeded on a receptor-modified (e.g., fibronectin-coated) cover glass to form adhesion complexes (e.g., clusters of adhesion molecules such as integrins, syndecans, and cadherins). The cover glass is then mounted to rotary arm 120 and cells are monitored during rotation. The magnitude of centrifugal force that detaches cells from the cover glass indicates the maximum adhesion strength of the adhesion complexes.

4.7 Example VII

Another application of spinning force system 100 relates to using system 100 in conjunction with other detection or measurement techniques (e.g., various kinds of single-molecule force probes or fluidic systems) to obtain force-related characteristics of the sample. For example, system 100 can be combined with a magnetic system to apply both magnetic and centrifugal forces to manipulate a test subject. A biotin labeled magnetic bead can be first pulled by a magnetic force toward a cell membrane (or a streptavidin-treated surface) to form a biotin-streptavidin attachment. The strength of this attachment can then be tested by applying a centrifugal force that pulls the bead away from the membrane.

System 100 can also be combined in use with devices that apply various types of chemical stimuli (e.g., chemoattractants and enzymes) and mechanical stimuli (e.g., compression, extension, and shearing) to a test subject, simulating the native environment of the subject during observation. For example, when system 100 is used for measuring the mechanical properties (e.g., elasticity or viscoelasticity) of endothelial cells, during spinning, a laminar or cyclic shear stress may also be provided to mimic the conditions of the endothelial cells in vivo. Additionally, cellular response to chemical/mechanical stimuli may also be observed.

4.8 Other Examples

In addition to detecting characteristics of biomolecular or chemical interactions, system 100 is also suitable for use with a wide range of general testing tasks. Examples include 1) measuring the mechanical properties of polymer networks or aggregates, where the overall behavior of the network may be of interest; 2) testing the strength and other characteristics of physical bonds formed between a subject and a surface; and 3) observing the behavioral changes of test subjects effected by chemical agents (e.g., an enzyme slicing a single DNA between two surfaces or urea denaturing a protein).

The use of a fiber optic rotary joint with small-scale system 1400 is generally useful for communicating with rotating samples, for instance for applications related to monitoring blood sorting.

5 Alternative Embodiments

Many variations of spinning force system 100 are possible.

Figure 8:
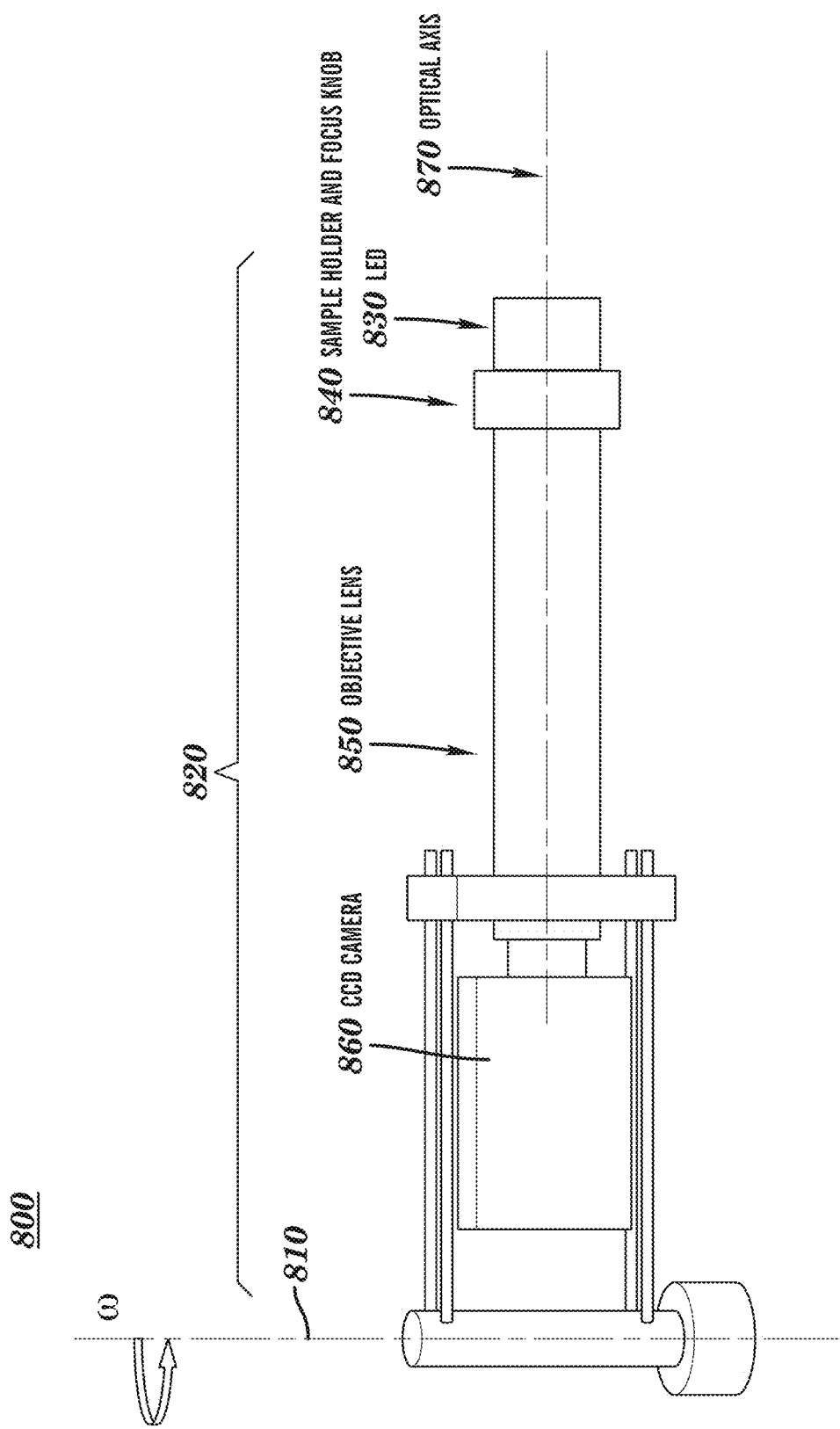
FIG. 8 shows an alternative embodiment (schematic in part) of the spinning force system of FIG. 1.

Referring to FIG. 8, an alternative embodiment of spinning force system 800 includes a coaxial detection assembly 820 mechanically coupled to a rotary stage 810. Detection assembly 820 includes a LED lamp 830, a sample holder 840, an objective lens 850, and a CCD camera 860, each being coaxially aligned with optical axis 870. LED lamp 830 is integrated into sample holder 840, which can be translated (e.g., along optical axis 870) through a focus knob for coarse adjustment. Fine adjustment of the position of sample holder 840 can be performed using a piezoelectric stage coupled to the holder (not shown). When rotary stage 810 operates in circular motion at angular velocity .omega., the entire detection assembly 820 rotates at .omega.

In some implementations, detection assembly 820 may be miniaturized to fit inside a standard centrifuge, eliminating the need for rotary stage 810 and reducing system cost.

Figure 9:
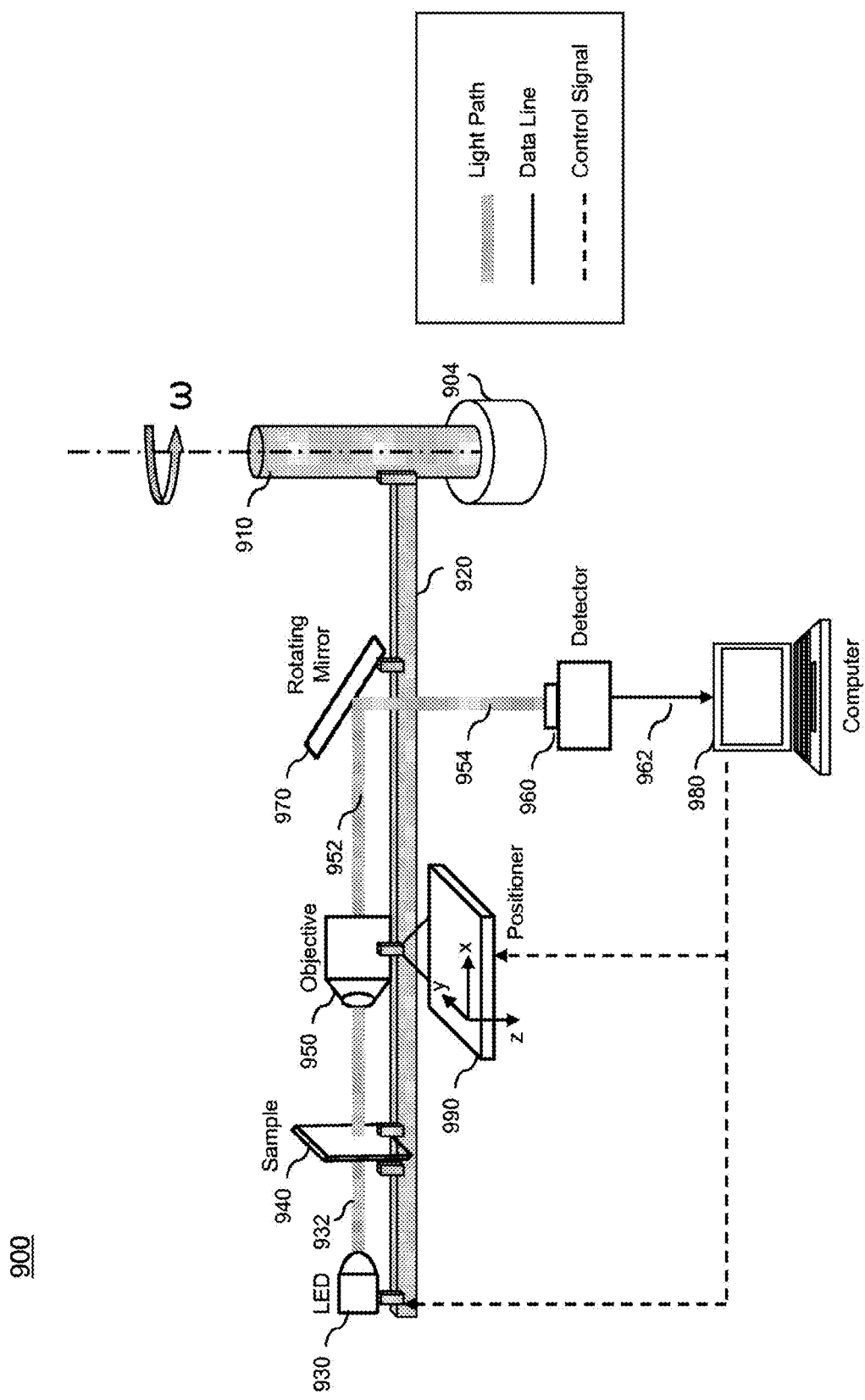
FIG. 9 shows an additional alternative embodiment of the spinning force system of FIG. 1.

Referring to FIG. 9, another alternative embodiment of spinning force system 900 is shown. Unlike detector 160 in system 100, detector 960 in this example is not mounted on rotary arm 920. Rather, detector 960 remains immobile during operation of system 900. Light from objective 950 are directed by a rotating mirror 970 to detector 960 through light paths 952 and 954 subsequently. Rotating mirror 970 is not necessarily mounted on rotary arm 920. For example, mirror 970 can be coupled to a separate rotor (not shown) or directly coupled to rotary stage 910 in order to reflect light from the rotating objective 950 to the stationary detector 960.

In the above examples of FIGS. 1, 8, and 9, the samples are detected using trans-illumination imaging techniques. More specifically, in FIG. 1, light 132 emitted from LED 130 transmits (penetrates) through sample 140 prior to being received by objective 150. In other examples, epi-illumination imaging techniques can also be conveniently used.

Figure 10:
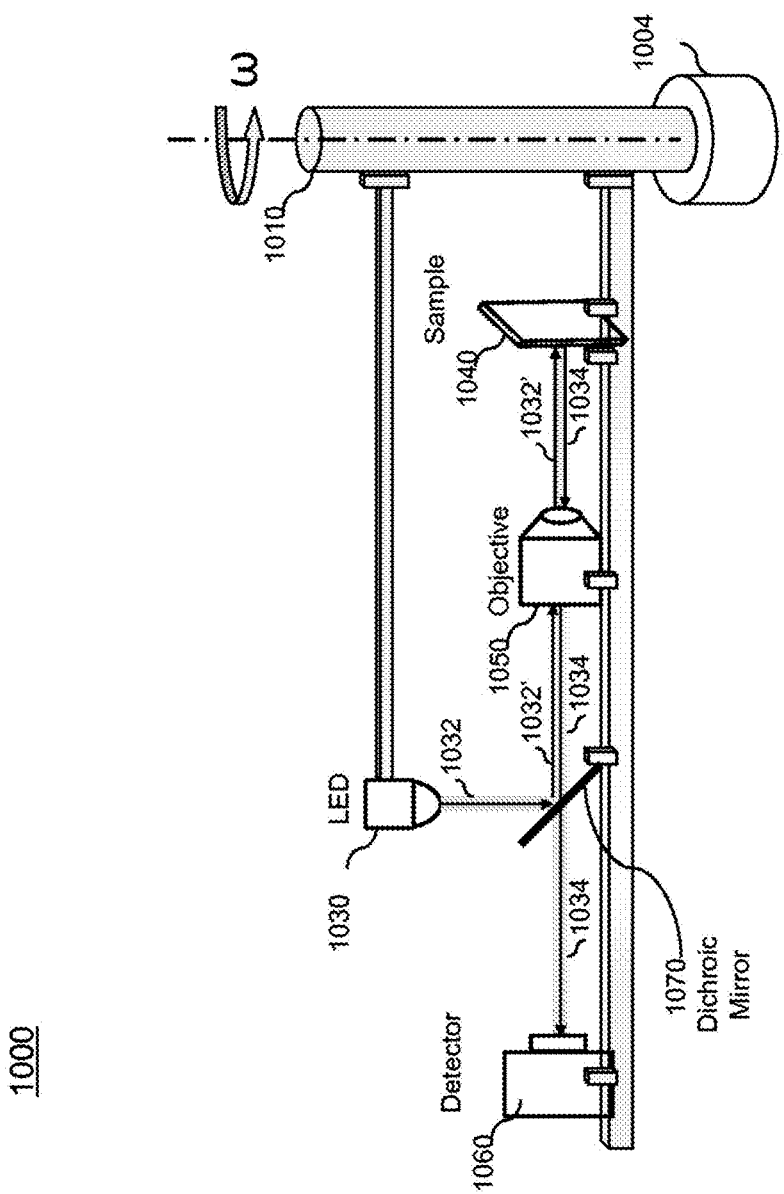
FIG. 10 shows a further alternative embodiment of the spinning force system of FIG. 1.

Referring to FIG. 10, a further alternative embodiment of spinning force system 1000 with epi-illumination is shown. Here, a Dichroic mirror 1070 is positioned between detector 1060 and objective 1050, serving as a beam splitter that directs light beams of different characteristics (e.g., different wavelengths) onto different paths. For example, light beam 1032 from LED 1030 is first deflected by Dichroic mirror 1070 towards objective 1050 (along light path 1032') to illuminate a selected region of sample 1040. A light beam 1034 is reflected from sample 1040 as a result of the illumination, travelling in a direction opposite to light beam 1032'. After passing through objective 1050 and Dicroic Mirror 1070, light beam 1034 is received by detector 1060 to produce an image of the illuminated region of sample 1040. In this example, objective 1050 serves as both a light condenser and an imaging lens.

In some embodiments, a vertical swinging or radially movable arm may be integrated to system 100 to enhance the flexibility of force control. System 100 may also be multiplexed to have many arms, each configured to carry a unique experiment. Each arm may also have a different and possibly adjustable length to facilitate force control.

In another embodiment, the samples are detected using surface plasmon resonance techniques. For instance, referring to the example of FIGS. 5A-5D, a baseline surface plasmon resonance signal is detected for the initial configuration of FIG. 5A, in which only molecules A 512 are present on the surface of the sample. As glass beads 520 are attached to the surface of the sample via interactions between molecules A 512 and B 522, the surface plasmon resonance signal increases. When the sample is rotated in spinning force system 100, a centrifugal force F is applied to bead 520. The rupture of interaction 530, which releases bead 520 from the surface of the sample, causes a decrease in the surface plasmon resonance signal. The detection of the surface plasmon resonance allows for the study of properties such as the binding constant between molecule A and molecule B.

It is to be understood that the foregoing description is intended to illustrate and not to limit the scope of the invention, which is defined by the scope of the appended claims. Other embodiments are within the scope of the following claims.

It is to be understood that the above description is intended to be illustrative, and not restrictive. For example, the above-described embodiments and/or aspects thereof may be used in combination with each other. In addition, many modifications may be made to adapt a particular situation or material to the teachings of the various embodiments without departing from their scope.

While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions, or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

This written description uses examples in the present disclosure, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A centrifuge force microscope module for use within a bucket rotatable away from and around an axis of a centrifuge in measuring a characteristic of a sample under a centrifugal force and/or in monitoring a sample under a centrifugal force, said centrifuge force microscope module comprising:
   an electrical module comprising:
      a housing removably disposable, configured, and supportable in the bucket of the centrifuge;
      at least one of a power source operably attached to said housing and disposed in the bucket and a connector operably attached to said housing and operably connectable to a power source disposable in the bucket for powering said electrical module;
   an optical module comprising:
      a detector operable to receive light from the sample;
      said optical module releasably connectable to said housing of said electrical module and disposable in the bucket of the centrifuge; and
   wherein said at least one of said power source and the power source in said electrical module is operable to power said detector.

2. The centrifuge force microscope module of claim 1 wherein said electrical module comprises an electrical contact for operably electrically grounding said centrifuge force microscope module through the bucket to the centrifuge.

3. The centrifuge force microscope module of claim 1 wherein said electrical module further comprises a transmitter and/or a receiver disposed in said housing and powered by said at least one of said power source and the power source in said electrical module, and said electrical module comprises an electrical contact for operably electrically connecting said centrifuge force microscope module through the bucket to the centrifuge so that the bucket and/or the centrifuge act as an antenna.

4. The centrifuge force microscope module of claim 1 wherein said optical module comprises a support for use in supporting the sample.

5. The centrifuge force microscope module of claim 1 wherein said electrical module is releasably electrically connectable to said detector.

6. The centrifuge force microscope module of claim 1 wherein said electrical module comprises a light source operable to illuminate the sample.

7. The centrifuge force microscope module of claim 1 wherein said housing comprises at least one upper opening for receiving said optical module therein.

8. The centrifuge force microscope module of claim 1 wherein said optical module comprises a U-shaped optical module comprising a first leg and a spaced-apart second leg, and said legs of said optical module being removably receivable in said housing.

9. The centrifuge force microscope module of claim 8 wherein said optical module comprises a first 45-degree turning mirror disposed at a base of said first leg and a second 45-degree turning mirror disposed at a base of said second leg.

10. The centrifuge force microscope module of claim 1 wherein said housing comprises releasably attachable upper and lower housing portions.

11. The centrifuge force microscope module of claim 10 wherein said lower portion of said housing comprises a light source.

12. The centrifuge force microscope module of claim 10 wherein said lower portion of said housing comprises said at least one of said power source and said connector operably connectable to the power source.

13. The centrifuge force microscope module of claim 1 wherein said housing comprises a side opening alignable with an opening in said optical module for accessing the sample.

14. The centrifuge force microscope module of claim 1 wherein said electrical module comprises a charging port disposed on said housing.

15. The centrifuge force microscope module of claim 1 further comprising a counterweight module.

16. The centrifuge force microscope module of claim 15 wherein the counterweight module comprises a plurality of holders and removable weights.

17. The centrifuge force microscope module of claim 1 further comprising the bucket and the centrifuge.

18. The centrifuge force microscope module of claim 1 wherein the centrifuge has an axis of rotation, and said optical module comprises an optical axis, said optical axis being generally parallel to the direction of a centrifugal force when said centrifuge force microscope module disposed in the bucket and the bucket is rotated about the axis of rotation of the centrifuge.

19. A centrifuge force microscope module for use within a bucket rotatable away from and around the axis of a centrifuge in measuring a characteristic of a sample under a centrifugal force and/or in monitoring a sample under a centrifugal force, said centrifuge force microscope module comprising:
   an electronics module-removably disposable, configured, and supportable in the bucket of the centrifuge, said electronics module comprising:
      a housing;
      a light source for illuminating the sample;
      a processor;
      at least one of a power source operably attached to said housing and disposed in the bucket and a connector operably attached to said housing and operably connectable to a power source disposable in the bucket for powering said electronics module;
   an optical module removably positionable in said housing and disposable in the bucket of the centrifuge, said optical module comprising:
      a detector operable to receive light from the sample;
      at least one optical lens for focusing the light from the sample onto said detector; and
   wherein said at least one of said power source and the power source in said electronics module is operable to power said light source, said detector, and said processor.

20. The centrifuge force microscope module of claim 19 wherein said housing comprises releasably attachable lower and upper housing portions.

21. The centrifuge force microscope module of claim 20 wherein said lower portion of said housing comprises said light source.

22. The centrifuge force microscope module of claim 21 wherein said lower portion of said housing is electrically connectable to said upper housing portion.

23. The centrifuge force microscope module of claim 19 wherein said electronics module comprises an electrical contact for operably electrically grounding said centrifuge force microscope module through the bucket to the centrifuge.

24. The centrifuge force microscope module of claim 19 wherein said electronics module further comprises a transmitter and/or a receiver, and said electronics module comprises an electrical contact for operably electrically connecting said centrifuge force microscope module through the bucket to the centrifuge so that the bucket and/or the centrifuge act as an antenna.

25. The centrifuge force microscope module of claim 19 wherein optical module comprises a U-shaped optical module comprising a first leg and a spaced-apart second leg, and said legs of said optical module being removably receivable in said housing.

26. A method for measuring a characteristic of a sample under a centrifugal force and/or use in monitoring a sample under a centrifugal force, the method comprising:
  rotating the sample in the centrifuge force microscope module of claim 1 in a bucket of a centrifuge about an axis to apply a centrifugal force on the sample;
  projecting light onto the rotating sample;
  detecting light emitted from the rotating sample; and
  at least one of measuring the characteristic of the sample under the centrifugal force and/or monitoring the sample under a centrifugal force.

27. A method for measuring a characteristic of a sample under a centrifugal force and/or use in monitoring a sample under a centrifugal force, the method comprising:
  rotating the sample in the centrifuge force microscope module of claim 19 in a bucket of a centrifuge about an axis to apply a centrifugal force on the sample;
  projecting light onto the rotating sample;
  detecting light emitted from the rotating sample; and
  at least one of measuring the characteristic of the sample under the centrifugal force and/or monitoring the sample under a centrifugal force.

28. A method for operating a centrifuge force microscope system disposed in a bucket of a centrifuge for measuring a characteristic of a sample under a centrifugal force and/or for monitoring a sample under a centrifugal force, the method comprising:
  providing the centrifuge force microscope module of claim 1;
  establishing a connection between the centrifuge force microscope module disposed in the bucket of the centrifuge and a remote computing unit;
  sending instructions from the remote computing unit to the centrifuge force microscope module regarding obtaining data from the sample; and
  transferring the obtained data from the centrifuge force microscope module to the remote computing unit.

29. The method of claim 28 wherein the establishing the connection comprises establishing a wireless connection, sending instructions comprises wirelessly sending the instructions, and the transferring comprises wirelessly transferring the obtained data.

30. The method of claim 28 wherein the sending instructions comprises at least one of camera frames to collect, location for store files, frame rate, and/or resolution.

31. The method of claim 28 wherein the transferring comprises wirelessly transferring the data automatically upon completion of an experiment.

32. The method of claim 28 further comprising controlling operation of the centrifuge using at least one of the centrifuge force microscope module and the remote computing unit.

33. The method of claim 28 further comprising turning on the centrifuge force microscope module.

34. The method of claim 33 wherein the turning on the centrifuge force microscope module comprise turning on a processor, powering a camera, powering a light source, establishing communication link between the processor and camera.

* * * * *